US007482483B2

(12) United States Patent
Sebti et al.

(10) Patent No.: US 7,482,483 B2
(45) Date of Patent: Jan. 27, 2009

(54) GROWTH FACTOR-BINDING COMPOUNDS AND METHODS OF USE

(75) Inventors: Said M. Sebti, Tampa, FL (US); Andrew D. Hamilton, Guildford, CT (US); Rishi Jain, Cambridge, MA (US)

(73) Assignees: University of South Florida, Tampa, FL (US); Yale University, New Haven, CT (US)

( * ) Notice: Subject to any disclaimer, the term of this patent is extended or adjusted under 35 U.S.C. 154(b) by 572 days.

(21) Appl. No.: 11/044,980

(22) Filed: Jan. 27, 2005

(65) Prior Publication Data

US 2005/0197401 A1    Sep. 8, 2005

Related U.S. Application Data

(60) Provisional application No. 60/539,613, filed on Jan. 27, 2004.

(51) Int. Cl.
*C07C 229/00* (2006.01)
*A61K 31/195* (2006.01)
(52) U.S. Cl. ..................... 562/450; 514/563
(58) Field of Classification Search ........... 514/563; 562/450
See application file for complete search history.

(56) References Cited

U.S. PATENT DOCUMENTS

| 5,496,846 | A | * | 3/1996 | Wilson et al. ............... 514/449 |
| 5,665,890 | A | | 9/1997 | Jacobsen et al. |
| 5,770,380 | A | | 6/1998 | Hamilton et al. |
| 5,929,232 | A | | 7/1999 | Jacobsen et al. |
| 6,054,297 | A | * | 4/2000 | Carter et al. ............... 435/69.6 |
| 6,262,257 | B1 | | 7/2001 | Gale et al. |
| 6,262,278 | B1 | | 7/2001 | Jacobsen et al. |
| 6,448,414 | B1 | | 9/2002 | Jacobsen et al. |
| 6,521,561 | B1 | | 2/2003 | Jacobsen et al. |
| 6,800,766 | B2 | | 10/2004 | Jacobsen et al. |
| 6,841,667 | B2 | | 1/2005 | Jacobsen et al. |
| 6,844,448 | B2 | | 1/2005 | Jacobsen et al. |
| 2002/0032338 | A1 | | 3/2002 | Jacobsen et al. |
| 2003/0118589 | A1 | | 6/2003 | Sebti et al. |
| 2003/0139614 | A1 | | 7/2003 | Jacobsen et al. |
| 2003/0187249 | A1 | | 10/2003 | Jacobsen et al. |
| 2004/0044233 | A1 | | 3/2004 | Jacobsen et al. |
| 2005/0187392 | A1 | | 8/2005 | Jacobsen et al. |
| 2005/0209471 | A1 | | 9/2005 | Jacobsen et al. |
| 2006/0084596 | A1 | | 4/2006 | Sebti et al. |

FOREIGN PATENT DOCUMENTS

| AT | 316950 | 2/2006 |
| AU | 9653639 | 10/1996 |
| CA | 2329316 | 11/1999 |
| CA | 2339618 | 2/2000 |
| CA | 2213007 C | 1/2004 |
| EP | 817765 A1 | 1/1998 |
| EP | 1073613 | 2/2001 |
| EP | 1104395 | 6/2001 |
| JP | 2002522515 | 7/2002 |
| NO | 9704234 | 11/1997 |
| WO | WO 9628402 | 9/1996 |
| WO | WO 97/37995 A1 | 10/1997 |
| WO | WO 9737995 | 10/1997 |
| WO | WO 9956699 A2 | 11/1999 |
| WO | WO 0009463 | 2/2000 |
| WO | WO 01/70930 A2 | 9/2001 |
| WO | WO 0170930 | 9/2001 |
| WO | WO 03/059925 A1 | 7/2003 |
| WO | WO 03059925 | 7/2003 |
| WO | WO 2005/072779 A2 | 8/2005 |

OTHER PUBLICATIONS

Andersson, M. et al. "Involvement of loop 2 of platelet-derived growth factor-AA and -BB in receptor binding" *Growth Factors*, 1995, 12:159-164.

Bergers, G. et al. "Benefits of targeting both pericytes and endothelial cells in the tumor vasculature with kinase inhibitors" *J Clin Invest*, 2003, 111:1287-1295.

Blaskovich, M.A. et al. "Design of GFB-111, a platelet-derived growth factor binding molecule with antiangiogenic and anticancer activity against human tumors in mice" *Nat Biotechnol*, 2000, 18:1065-1070.

Dvorak, H.F. et al. "Vascular permeability factor/vascular endothelial growth factor and the significance of microvascular hyperpermeability in angiogenesis" *Curr Top Microbiol Immunol*, 1999, 237:97-132.

Dvorak, H.F. "Vascular permeability factor/vascular endothelial growth factor: a critical cytokine in tumor angiogensis and a potential target for diagnosis and therapy" *J Clin Oncol*, 2002, 20:4368-4380.

Eriksson, U. and Alitalo, K. "Structure, expression and receptor-binding properties of novel vascular endothelial growth factors" *Curr Top Microbiol Immunol*, 1999, 237:41-57.

Ferrara, N. "Vascular endothelial growth factor: molecular and biological aspects" *Curr Top Microbiol Immunol*, 1999, 237:1-30.

Ferrara, N. "Role of vascular endothelial growth factor in physiologic and pathologic angiogenesis: therapeutic implications" *Semin Oncol*, 2002, 29:10-14.

(Continued)

*Primary Examiner*—Rita J. Desai
*Assistant Examiner*—John Mabry
(74) *Attorney, Agent, or Firm*—Dickstein Shapiro LLP

(57) ABSTRACT

Growth factor binding compounds having a plurality of acyclic isophthalic acid groups attached to a non-peptide organic scaffold and pharmaceutical compositions of the same are disclosed. Methods of administering and using the growth factor binding compounds or the growth factor binding compositions are also taught. These novel growth factor binding compounds are useful for treating angiogenesis, excessive cellular proliferation, tumor growth, and a combination thereof as well as inhibiting growth factor binding to cells and phosphorylation.

8 Claims, 12 Drawing Sheets

OTHER PUBLICATIONS

Jain, R.K. "Tumor angiogenesis and accessibility: role of vascular endothelial growth factor" *Semin Oncol*, 2002, 29:3-9.

Kerbel, R.S. "Tumor angiogenesis: past, present and the near future" *Carcinogenesis*, 2000, 21:505-515.

Laird, A.D. et al. "SU6668 is a potent antiangiogenic and antitumor agent that induces regression of established tumors" *Cancer Res*, 2000, 60:4152-4160.

Miao, R.Q. et al. "Kallistatin is a new inhibitor of angiogenesis and tumor growth" *Blood*, 2002, 100:3245-3252.

Morin, M.J. "From oncogene to drug: development of small molecule tyrosine kinase inhibitors as anti-tumor and anti-angiogenic agents" *Oncogene*, 2000, 19:6574-6583.

Oefner, C. et al. "Crystal structure of human platelet-derived growth factor BB" *Embo J*, 1992, 11:3921-3926.

Sebti, S. and Hamilton, A.D. "Design of growth factor antagonists with antiangiogenic and antitumor properties" *Oncogene*, 2000, 19(56):6566-6573.

Sun, J. et al. "Inhibiting angiogenesis and tumorigenesis by a synthetic molecule that blocks binding of both VEGF and PDGF to their receptors" *Oncogene*, 2005, pp. 1-9.

Sun, J. et al. "Inhibiting angiogenesis and tumorigenesis by a synthetic molecule that blocks binding of both VEGF and PDGF to their receptors" presented at Annual Meeting of the American Association for Cancer Research, Mar. 26-30, 2004, Orlando, FL, abstract No. 4533.

Sun, J. et al. "Blocking angiogenesis and tumorigenesis with GFA-116, a synthetic molecule that inhibits binding of vascular endothelial growth factor to its receptor" *Cancer Res*, May 15, 2004, 64(10):3586-3592.

Wedge, S.R. et al. "ZD4190: an orally active inhibitor of vascular endothelial growth factor signaling with broad-spectrum antitumor efficacy" *Cancer Res*, 2000, 60:970-975.

Zhang, W. et al. "A monoclonal antibody that blocks VEGF binding to VEGFR2 (KDR/Flk-1) inhibits vascular expression of Flk-1 and tumor growth in an orthotopic human breast cancer model" *Angiogenesis*, 2002, 5:35-44.

Lin, Q. and Hamilton, A. "Design and synthesis of multiple-loop receptors based on a calix[4]arene scaffold for protein surface recognition" *C.R. Chimie*, 2002, 5:441-450.

Shuker, S. et al. "Solid-phase synthesis of a novel peptide substituted calix[4]arene" *Synlett*, 2001, 2:210-213.

International Search Report PCT/US01/08920, dated Aug. 31, 2001.

Bach, A.C. et al. "Structural studies of a family of high affinity ligands for GPIIb/IIIa" *J. Am. Chem. Soc.*, 1994, 116:3207-3219.

Hamuro, Y. et al. "A calixarene with four peptide loops: an antibody mimic for recognition of protein surfaces" *Agnew. Chemie Int. Ed. Engl.*, 1997, 36:2680-2683.

Lin, Q. et al. "Protein surface recognition by synthetic agents: Design and structural requirements of a family of artificial receptors that bind to cytochrome c" *Biopoly*, 1998, 47:285-297.

Park, H.D. et al. "Protein surface recognition by synthetic receptors: a route to novel sub-micromolar inhibitors for chymotrypsin" *J. Am. Chem. Soc.*, 1999, 121:8-13.

Wilson, I.A. et al. "Structural aspects of antibodies and antibody-antigen complexes" *Ciba Foundation Symp.*, 1991, 159:13-39.

Sun, Jiazhi et al., Inhibiting angiogenesis and tumorigenesis by a synthetic molecule that blocks binding of both VEGF and PDGF to their receptors, Oncogene (2005), 24(20), 4701-4709, Nature Publishing Group, USA.

Sun, Jiazhi et al., Inhibiting angiogenesis and tumorigenesis by a synthetic molecule that blocks binding of both VEGF and PDGF to their receptors, Proc.Am.Assoc. Cancer Res. (95 Meet., 1046-47, 2004), USA.

Blaskovich M A et al.; Design of GFB-111, a platelet-derived growth factor binding molecule with antiangiogenic and anticancer activity against human tumors in mice, Nature Biotechnology, Nature Publishing, Oct. 2000, vol. 18, No. 10, pp. 1065-1070, United States.

Examination Report issued on May 21, 2007 by European Patent Office for European Application No. 05722650.8.

European Patent Office, Examination Report issued Feb. 27, 2008.

* cited by examiner

GROWTH FACTOR-BINDING COMPOUNDS AND METHODS OF USE

CROSS-REFERENCE TO RELATED APPLICATION

The present application claims benefit of U.S. Provisional Application Ser. No. 60/539,613, filed Jan. 27, 2004, which is hereby incorporated by reference herein in its entirety, including any figures, tables, nucleic acid sequences, amino acid sequences, and drawings.

The subject invention was made with government support under a research project supported by National Institute of Health/National Cancer Institute Grant No. CA78038. The federal government may have certain rights in this invention.

BACKGROUND OF THE INVENTION

The ability of tumors to grow beyond a few cubic millimeters in volume depends on the formation of new blood vessels within the microenvironment of the tumors (Ferrara, N. *Nat Rev Cancer,* 2002, 2:795-803; Kerbel, R. S. *Carcinogenesis,* 2000, 21:505-15; Carmeliet, P. and Jain, R. K. *Nature,* 2000, 407:249-57; Yancopoulos, G. D. et al. *Nature,* 2000, 407:242-8). This angiogenic process is triggered by several key growth factors that are secreted by the tumor. The growth factors not only bind their receptors on endothelial cells and stimulate their proliferation initiating new blood vessel formation, but also bind receptors on accessory cells such as pericytes that maintain vessel integrity (Ferrara, N. *Nat Rev Cancer,* 2002, 2:795-803; Kerbel, R. S. *Carcinogenesis,* 2000, 21:505-15; Carmeliet, P. and Jain, R. K. *Nature,* 2000, 407:249-57; Yancopoulos, G. D. et al. *Nature,* 2000, 407:242-8; Helmlinger, G., et al. *Nat Med,* 1997, 3:177-82; Holash, J. et al. *Science,* 1999, 284:1994-8). Among the most studied growth factors are vascular endothelial growth factor (VEGF) and platelet-derived growth factor (PDGF). Several studies have demonstrated the participation of these two growth factors in the angiogenic process with VEGF playing a key role mainly in the initiation of the formation of new blood vessels and PDGF being involved in the maintenance of these vessels (Bergers, G. et al. *J Clin Invest,* 2003, 111:1287-95; Dvorak, H. F. *J Clin Oncol,* 2002, 20:4368-80; Ferrara, N. *Curr Top Microbiol Immunol,* 1999, 237:1-30; Dvorak, H. F. et al. *Curr Top Microbiol Immunol,* 1999, 237:97-132; Eriksson, U. and Alitalo, K. *Curr Top Microbiol Immunol,* 1999, 237:41-57).

This observation prompted an interest in designing strategies to suppress the functions of VEGF and PDGF, with the ultimate goal of inhibiting angiogenesis and starving tumors. The approaches that have been taken were based on targeting the biochemical steps involved in the mechanism of action of these growth factors. These include inhibiting the binding of VEGF and PDGF to their respective receptors by using antibodies against the growth factors. One of these, AVASTIN, which targets VEGF, has recently been approved for clinical use in patients with metastatic colorectal cancer (Zhang, W. et al. *Angiogenesis,* 2002, 5:35-44; Ferrara, N. *Semin Oncol,* 2002, 29:10-4). Another approach has involved the development of inhibitors of the tyrosine kinase activities of the PDGF and VEGF receptors, resulting in suppression of the downstream signal transduction pathways triggered by these growth factors (Kerbel, R. S. *Carcinogenesis,* 2000, 21:505-15; Jain, R. K. *Semin Oncol,* 2002, 29:3-9; Morin, M. J. *Oncogene,* 2000, 19:6574-83; Miao, R. Q. et al. *Blood,* 2002, 100:3245-52; Laird, A. D. et al. *Cancer Res,* 2000, 60:4152-60; Wedge, S. R. et al. *Cancer Res,* 2000, 60:970-5). Most of these agents mimic the structure of ATP and some are potent antitumor agents that are presently in clinical trials. However, none have been approved yet by the FDA.

The approval by the FDA of AVASTIN (bevacizumab), which increases by 5 months the median survival of patients with metastatic colorectal cancer, further validates targeting angiogenic processes as a strategy to treat cancer (Ferrara, N. *Semin Oncol,* 2002, 29:10-4). However, much more needs to be done to fully exploit this approach. For example, in other clinical trials, AVASTIN failed to prolong the lives of patients with metastatic breast cancer. One possible explanation for this inconsistent activity is that advanced metastatic breast cancer may circumvent anti-VEGF angiogenesis therapy by means of other growth factors. Indeed support for this suggestion comes from preclinical studies showing that early breast cancer secretes mainly VEGF whereas advanced breast cancer secretes additional growth factors (Relf, M. et al. *Cancer Res,* 1997, 57:963-9). Furthermore, in an animal pancreatic cancer model, SU5416, a VEGF receptor tyrosine kinase inhibitor suppresses early, but not late, development of pancreatic tumors. More importantly in the same model, treatment with SU6668 (which inhibits both VEGF and PDGF receptor tyrosine kinases) induced regression of advanced pancreatic tumor at late stage of development (Bergers, G. et al. *J Clin Invest,* 2003, 111:1287-95) suggesting that the failure of anti-VEGF therapy may be due to its ability to inhibit only initiation but not maintenance of blood vessels. Further support for this suggestion comes from a very recent study where AVASTIN inhibited the formation of new blood vessels but was ineffective at inhibiting already established ones in an animal model where neuroblastoma cells were transplanted onto mouse kidneys (Huang, J. et al. *Proc Natl Acad Sci USA,* 2003, 100:7785-90). Taken together, the present understanding of the angiogenesis process suggests that simultaneously targeting of growth factors that initiate (i.e., VEGF) as well as those that maintain (i.e., PDGF) blood vessels may be a more effective approach to cancer therapy than targeting only one growth factor.

BRIEF SUMMARY OF THE INVENTION

It is an object of the subject invention to design a family of compounds that bind VEGF and/or PDGF and inhibit the binding of these growth factors to their respective cell surface receptors. For example, the compound GFB204, was found to be a potent and selective inhibitor of VEGF- and PDGF-stimulation of their receptor tyrosine kinase phosphorylation and signaling (Erk1/2, Akt and STAT3). This pharmacological agent also potently inhibited endothelial cell migration and capillary network formation in vitro as well as in vivo blood vessel formation and human tumor growth in nude mouse xenografts.

It is a further object of the subject invention to provide pharmaceutical compositions of the above-referenced family of compounds and methods of administering the same.

BRIEF DESCRIPTION OF THE DRAWINGS

FIGS. 2A-2C show specific binding (% control) for PDGFR, Flk-1, and EGFR, respectively.

FIGS. 7A and 7B Microvessel Count; FIG. 7A=11.3±1.9; FIG. 7B=2.6±0.9.

MATERIALS AND METHODS

Figure 1:
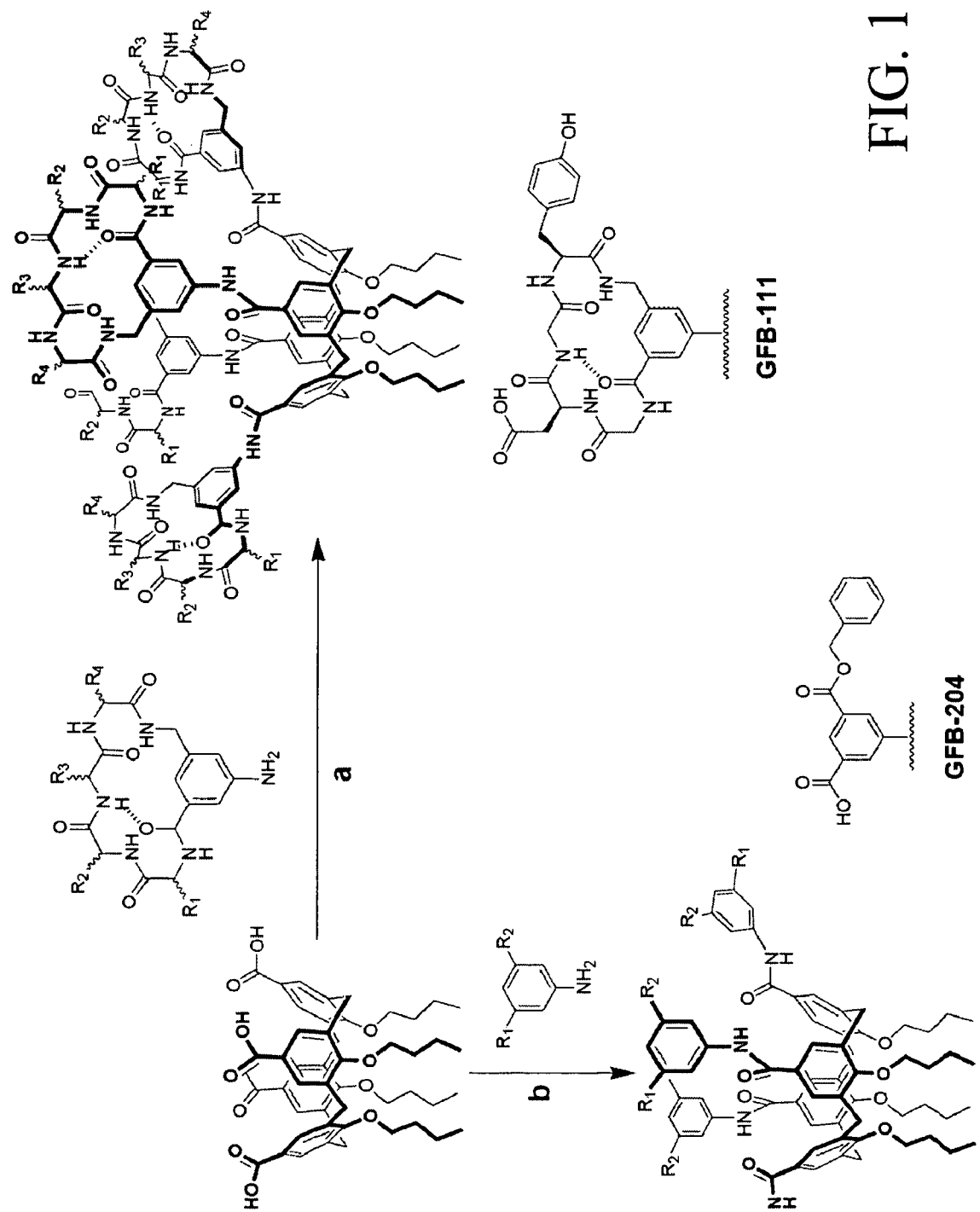
FIG. 1 shows structures of GFB204 of the present invention, which have acyclic isophthalic acid groups attached to a non-peptide organic scaffold as well as GFB-111.

Inhibition of Growth Factor-Dependent Receptor Tyrosine Phosphorylation by GFBs.

Starved Flk-1/KDR-overexpressing NIH 3T3 cells (Flk-1/NIH 3T3) or NIH 3T3 cells were pretreated with GFBs for 5 min before stimulation with VEGF (50 ng/ml) or PDGF-BB (10 ng/ml) for 10 min, respectively. The cells were then harvested and lysed, and proteins from the lysates were separated by SDS-PAGE and transferred to nitrocellulose. Membranes then were either immunoblotted with anti-phospho-VEGFR2 antibody (Cell Signaling Technologies, Beverly, Mass.) for activated Flk-1 or anti-phospho-tyrosine antibody (4G10, Upstate Biotechnology, Lake Placid, N.Y.) for activated PDGFR. Phosphotyrosine Flk-1 and PDGFR were quantified using a Bio-Rad Model GS-700 Imaging Densitometer (Bio-Rad Laboratories, Inc, Hercules, Calif.) (Blaskovich, M. A. et al. *Nat Biotechnol*, 2000, 18:1065-70).

Growth Factor-Mediated Stimulation of Phosphorylation of Erk1/2, Akt and STAT3.

Starved NIH 3T3 cells (PDGF-BB, bFGF), NIH 3T3 cells overexpressing EGFR (EGFR/NIH 3T3, EGF), Flk-1 (Flk-1/NIH 3T3, VEGF), and IGF-1R NIH 3T3 (IGF-1R/NIH 3T3, IGF-1) were pretreated with the indicated concentration of GFB204 for 5 minutes before 10 minute stimulation with PDGF-BB (10 ng/ml), EGF (10 ng/ml), bFGF (50 ng/ml), VEGF (50 ng/ml) and IGF-1 (50 ng/ml). Cell lysates were run on SDS-PAGE gels, then transferred to nitrocellulose and Western blotted with anti-phosphorylated Erk1/Erk2 (Cell Signaling Technologies) anti-phosphorylated Akt or anti-phosphorylated STAT3 as described previously by us (Blaskovich, M. A. et al. *Cancer Res*, 2003, 63:1270-9).

Binding of $^{125}$I-growth factors to their receptors. The binding assay of $^{125}$I-VEGF, $^{125}$I-PDGF and $^{125}$I-EGF to their respective receptors was carried out as described previously (Blaskovich, M. A. et al. *Nat Biotechnol*, 2000, 18:1065-70. Briefly, Flk-1/NIH 3T3 cells, NIH 3T3 cells and EGFR/NIH 3T3 cells were incubated with $^{125}$I-VEGF, $^{125}$I-PDGF and $^{125}$I-EGF (50,000 cpm/well), respectively, and increasing concentrations of GFB204. Cells were incubated at 4° C. for 0.5 hours, then washed three times with PBS and three times with 25 mM Tris, pH 8.0, 1% Triton-X-100, 10% glycerol, and 1% SDS prior to determining $^{125}$I counts on a gamma counter (Beckmann Inc.). An excess of cold growth factors were used to obtain nonspecific binding levels.

Capillary network formation. 200 Ξl of Matrigel was placed into each well of a 24-well culture plate at 4° C. and allowed to polymerize by incubation at 37° C. as described previously (Papadimitriou, E. et al. *Biochem Biophys Res Commun*, 2001, 282:306-13). Human middle cerebral artery endothelial cells (5×10$^4$) were seeded on the Matrigel in 1 ml of EBM containing VEGF (20 ng/ml). The cells were incubated in the presence or absence of GFB204 at the concentrations indicated in the figure legend. Each sample was photographed using a 10× objective lens, and quantified the total length of tube structures in each photograph using the Image Pro Plus software (Media Cybernetic, Inc., MD).

Human brain endothelial cell migration assay. Migration of adult human brain endothelial cells was evaluated using a modified Boyden chamber assay (BD BioCoat Matrigel Invasion Chamber) (Papadimitriou, E. et al. *Biochem Biophys Res Commun*, 2001, 282:306-13). The cells were plated at 4×10$^4$/ml onto an 8 µm pore size membrane coated with a thin layer of Matrigel basement membrane matrix. GFB204 was added to the medium in the outer chamber and the cells were cultured for 18 hours under VEGF-dependent condition in the lower chamber (VEGF 20 ng/ml). Non-invading cells were removed from the upper surface with a cotton swab. Membrane inserts were then fixed with 4% paraformaldehyde and stained with Crystal-Violet dye. The number of cells that migrated to the undersurface of the filters, was quantified by counting the cells migrated in randomly selected microscopic fields (10×). Samples were analyzed for significant differences using a Student's t-test for independent samples.

Antitumor activity in the nude mouse tumor xenograft model. Nude mice (Charles River, Wilmington, Mass.) were maintained in accordance with the Institutional Animal Care and Use Committee (IACUC) procedures and guidelines. A-549 cells were harvested and resuspended in PBS, then injected s.c. into the right and left flanks ($10 \times 10^6$ cells per flank) of 8 week old female nude mice as reported previously (Sun, J. et al. *Cancer Res*, 1999, 59:4919-26). When tumors reached about 100 mm$^3$, animals were dosed i.p. with 0.2 ml solution once daily. Control animals received a vehicle whereas treated animals were injected with GFB204 (1 or 5 mg/kg/day). The tumor volumes were determined by measuring the length (l) and the width (w) and calculating the volume ($V=1 \ w^2/2$) as described previously (Sun, J. et al. *Cancer Res*, 1999, 59:4919-26). Statistical significance between control and treated animals were evaluated using Student's t-test.

IHC study. On the termination day of antitumor experiments, the tumors were extracted and fixed in 10% neutral buffered formalin for 6 hours. After fixation, the tissue samples were processed into paraffin blocks. Tissue sections (4 μm thick) were obtained from the parablocks and stained with hematoxylin and eosin (H&E) using standard histological techniques. Tissue sections were also subjected to immunostaining for CD31 (BD Biosciences, San Diego, Calif.) using the avidin biotin peroxidase complex technique (Blaskovich, M. A. et al. *Nat Biotechnol*, 2000, 18:1065-70). Mouse monoclonal antibody was used at 1:50 dilution, following microwave antigen retrieval (four cycles of 5 minutes each on high in 0.1 M citrate buffer).

DETAILED DISCLOSURE OF THE INVENTION

The present invention pertains to growth factor-binding compounds. More particularly, the present invention pertains to compounds (such as those shown in Table 1) that bind growth factors such as VEGF and/or PDGF, and are capable of inhibiting the binding of one or more of these growth factors to their respective cell surface receptors. The invention also concerns pharmaceutical compositions comprising one or more of these compounds and a pharmaceutically acceptable carrier.

In addition, the present invention concerns methods for inhibiting the binding of such growth factors to cells by contacting one or more compounds of the invention (or compositions comprising one or more of the compounds) with the cells in vitro or in vivo. In other aspects, the present invention includes methods for inhibiting growth factor-stimulated phosphorylation (e.g., phosphorylation of Erk1, Erk2, Akt, and/or STAT3); methods for inhibiting angiogenesis; and methods for inhibiting cancer and/or tumor growth by contacting one or more compounds or compositions of the present invention with target cells in vitro or in vivo.

In a specific embodiment, the present invention concerns a method useful for inhibiting growth factors from binding to cells, for inhibiting growth factor stimulated phosphorylation, for inhibiting angiogenesis, for inhibiting cancer and tumor growth or a combination thereof, wherein the method comprises contacting at least one growth factor binding compounds or a pharmaceutically acceptable salt of any of the growth factor binding compounds, to a cell in vitro or in vivo; wherein the growth factor binding compounds comprise a plurality of acyclic isophthalic acid groups attached to a non-peptide organic scaffold; wherein each of the growth factor binding compounds, or the pharmaceutically salt of any of the growth factor binding compounds may or may not be carried in a pharmaceutically acceptable carrier, except for the compound having the general structure:

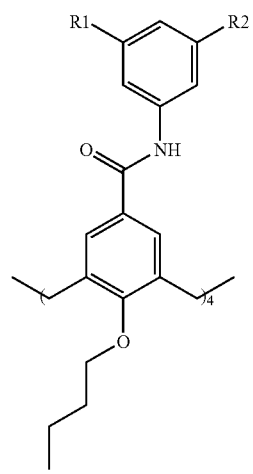

wherein each R1 is:

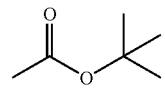

and each R2 is:

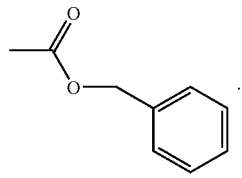

In a yet another specific embodiment, a pharmaceutical composition of the present invention is administered locally or systemically to a patient to achieve inhibition of angiogenesis, inhibition of tumor growth, and/or inhibition of cancer.

In one embodiment, the present invention includes a growth factor-binding compound comprising a plurality of acyclic isophthalic acid groups attached to a non-peptide organic scaffold. In a further embodiment, the organic scaffold is a calix[4]arene scaffold. Acyclic isophthalic acid groups of the compounds of the invention can be functionalized with an acidic group, a hydrophobic group, or both.

In another embodiment, the growth factor binding compound of the present invention has the general structure:

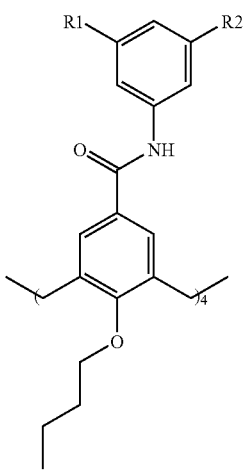

wherein each R₁ is independently selected from among the following chemical groups:

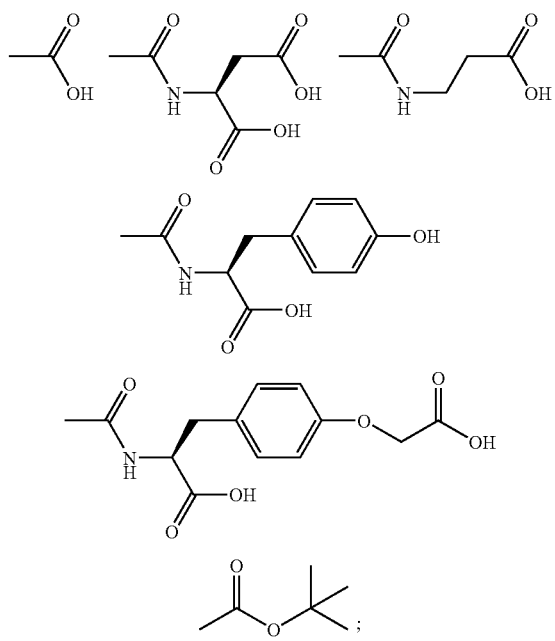

and each R₂ is independently selected from among the following chemical groups:

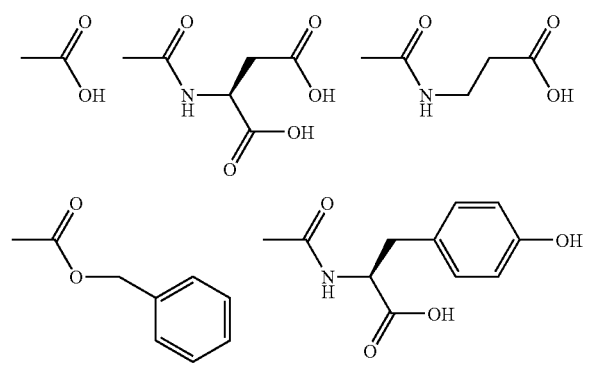

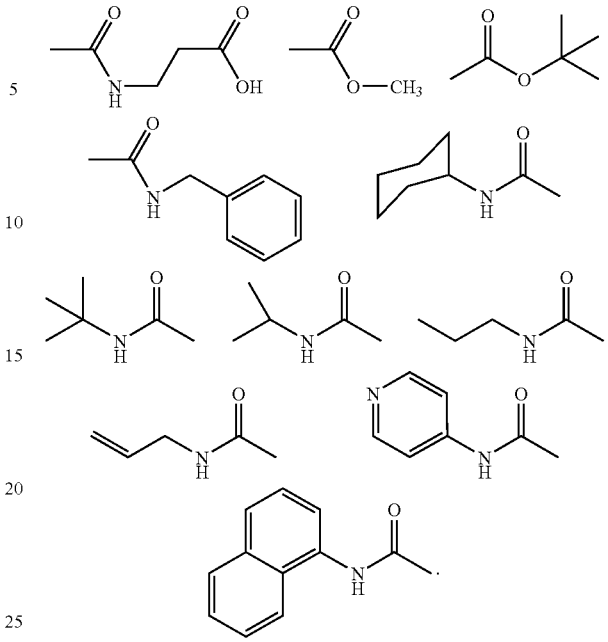

In specific embodiments, the compound of the present invention is selected from the group consisting of GFB201, GFB202, GFB203, GFB204, GFB205, GFB206, GFB207, GFB208, GFB209, GFB210, GFB211, GFB212, GFB213, GFB214, GFB215, GFB216, GFB217, GFB218, and GFB219 (as set forth in Table 1).

Growth factors that are targeted or acted upon by the compounds of the subject invention can include, but are not limited to, platelet derived growth factor, a vascular endothelial growth factor, or both.

In another aspect, the present invention provides a composition comprising at least one compound of the invention, as disclosed herein, or a pharmaceutically acceptable salt thereof; and a pharmaceutically acceptable carrier.

In another aspect, the present invention provides a method of treating a patient having a disease comprising excess cellular proliferation, excess angiogenesis, a tumor, or a combination of any of the foregoing, wherein the method comprises administering to the patient an effective amount of a compound or composition of the invention. In a specific embodiment, the tumor may express elevated amounts of a growth factor, such as platelet derived growth factor, vascular endothelial growth factor, or both. Also elevated levels of PDGF and VEGF could come from the tumor microenvironment due to angiogenic endothelial cells and vessels.

In yet another specific embodiment, the present invention provides a method for treating a patient having a disease comprising excess cellular proliferation, excess angiogenesis, a tumor, or a combination of any of the foregoing, wherein the method comprises administering an effective amount of a pharmaceutical composition, wherein the pharmaceutical composition comprises at least one growth factor binding compounds or a pharmaceutically acceptable salt of any of the growth factor binding compounds, and a pharmaceutically acceptable carrier; or one or more growth factor compounds, wherein the growth factor binding compounds comprise a plurality of acyclic isophthalic acid groups attached to a non-peptide organic scaffold except for the compound having the general structure:

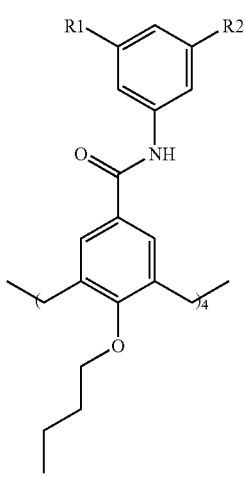

wherein each R1 is:

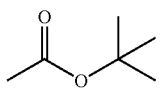

and each R2 is:

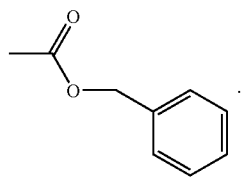

Formulations (also referred to herein as compositions) include those suitable for local or systemic administration, such as oral, rectal, nasal, topical (including transdermal, buccal and sublingual), vaginal, parenteral (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product. Formulations of the present invention suitable for oral administration can be presented as discrete units such as capsules, cachets or tablets, each containing a predetermined amount of the active ingredient; or as an oil-in-water liquid emulsion, water-in-oil liquid emulsion or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents.

Formulations suitable for topical administration to the eye also include eye drops wherein the active ingredient is dissolved or suspended in a suitable carrier, especially an aqueous solvent for the agent.

Formulations for rectal administration can be presented as a suppository with a suitable base comprising, for example, cocoa butter or a salicylate.

Formulation suitable for vaginal administration can be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns, which is administered in the manner in which snuff is taken, i.e., by rapid inhalation through the nasal passage from a container of the powder held close up to the nose. Suitable formulations wherein the carrier is a liquid for administration by nebulizer, include aqueous or oily solutions of the agent.

Formulations suitable for parenteral administration include aqueous and non-aqueous isotonic sterile injection solutions that can contain antioxidants, buffers, bacteriostats and solutes which render the formulation isotonic with the blood of the intended recipient; and aqueous and non-aqueous sterile suspensions that can include suspending agents and thickening agents, and liposomes or other microparticulate systems that are designed to target the compound to blood components or one or more organs. The formulations can be presented in unit-dose or multi-does or multi-dose sealed containers, such as for example, ampoules and vials, and can be stored in a freeze-dried (lyophilized) condition requiring only the addition of the sterile liquid carrier, for example water for injections, immediately prior to use. Extemporaneous injection solutions and suspensions can be prepared from sterile powders, granules and tablets of the kind previously described.

Preferred unit dosage formulations are those containing a daily dose or unit, daily subdose, as herein above-recited, or an appropriate fraction thereof, of an agent. It should be understood that in addition to the ingredients particularly mentioned above, the formulations of this invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known and can be used to administer a compound of the invention, e.g., encapsulation in liposomes, microparticles, microcapsules, receptor-mediated endocytosis and the like. Methods of delivery include, but are not limited to, intra-arterial, intramuscular, intravenous, intranasal, and oral routes. In a specific embodiment, the pharmaceutical compositions of the invention can be administered locally to the area in need of treatment; such local administration can be achieved, for example, by local infusion during surgery, by injection, or by means of a catheter.

Therapeutic amounts can be empirically determined and will vary with the pathology being treated, the subject being treated, and the efficacy and toxicity of the agent. Similarly, suitable dosage formulations and methods of administering the agents can be readily determined by those of skill in the art.

The pharmaceutical compositions can be administered by any of a variety of routes, such as orally, intranasally, parenterally or by inhalation therapy, and can take form of tablets, lozenges, granules, capsules, pills, ampoule, suppositories or aerosol form. They can also take the form of suspensions, solutions, and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

Ideally, the agent should be administered to achieve peak concentrations of the active compound at sites of the disease. Peak concentrations at disease sites can be achieved, for example, by intravenously injecting of the agent, optionally in saline, or orally administering, example, a tablet, capsule or syrup containing the active ingredient.

Advantageously, the compositions can be administered simultaneously or sequentially with other drugs or biologically active agents, such as anti-cancer agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Preferably, the administering is carried out orally, parenterally, subcutaneously, intravenously, intramuscularly, intraperitoneally, intraarterially, transdermally or via a mucus membrane.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, prostate cancer, leukemia, hormone dependent cancers, breast cancer, colon cancer, lung cancer, epidermal cancer, liver cancer, esophageal cancer, stomach cancer, cancer of the brain, and cancer of the kidney.

The terms "treatment", "treating" and the like are intended to mean obtaining a desired pharmacologic and/or physiologic effect, e.g., inhibition of cancer cell growth or induction of apoptosis of a cancer cell. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing cancer) from occurring in an individual who may be predisposed to the disease but has not yet been diagnosed as having it; (b) inhibiting the disease, (e.g., arresting its development); or (c) relieving the disease (e.g., reducing symptoms associated with the disease).

The term "anti-cancer activity" is intended to mean an activity which is able to substantially inhibit, slow, interfere, suppress, prevent, delay and/or arrest a cancer and/or a metastasis thereof (such as initiation, growth, spread, and/or progression thereof of such cancer and/or metastasis).

The terms "administering", "administration", and "contacting" are intended to mean a mode of delivery including, without limitation, oral, rectal, parenteral, subcutaneous, intravenous, intramuscular, intraperitoneal, intraarterial, transdermally or via a mucus membrane. The preferred one being orally. Administration may be carried out locally, at a target site(s), or systemically. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

The term "therapeutically effective" is intended to mean an amount of a compound of the invention sufficient to substantially improve some symptom associated with a disease or a medical condition. For example, in the treatment of cancer, a compound which decreases, prevents, delays, suppresses, or arrests any symptom of the disease would be therapeutically effective. A therapeutically effective amount of a compound is not required to cure a disease but will provide a treatment for a disease such that the onset of the disease is delayed, hindered, or prevented, or the disease symptoms are ameliorated, or the term of the disease is changed or, for example, is less severe or recovery is accelerated in an individual.

The term "independently" is intended to mean that each of the four R1 substituents and each of the four R2 substituents of the growth factor binding compounds of the present invention may each be the same substituent or may each be a different substituent.

When the compounds of this invention are administered in combination therapies with other agents, they may be administered sequentially or concurrently to an individual. Alternatively, pharmaceutical compositions according to the present invention may be comprised of a combination of a compound of the present invention, as described herein, and another therapeutic or prophylactic agent known in the art.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

As used herein, the term "pharmaceutically acceptable carrier" includes any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions. The pharmaceutical compositions of the subject invention can be formulated according to known methods for preparing pharmaceutically useful compositions. Formulations are described in a number of sources which are well known and readily available to those skilled in the art. For example, *Remington's Pharmaceutical Science* (Martin E W (1995) Easton Pa., Mack Publishing Company, 19$^{th}$ ed.) describes formulations which can be used in connection with the subject invention.

As used herein, the terms "individual" and "patient" are used interchangeably to refer to any vertebrate species, such as humans and animals. Preferably, the patient is of a mammalian species. Mammalian species which benefit from the disclosed methods include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Human or non-human animal patients can range in age from neonates to elderly.

In accordance with another embodiment of the present invention, there is provided a method of treating cancer, comprising administering to an individual a pharmaceutically effective amount of a pharmaceutical composition of the present invention.

Preferably, a cancer to be treated in accordance with an embodiment of the present invention is selected from the group consisting of prostate cancer, leukemia, hormone dependent cancers, breast cancer, colon cancer, lung cancer, epidermal cancer, liver cancer, esophageal cancer, stomach cancer, cancer of the brain, and cancer of the kidney.

EXAMPLE 1

Identification of GFB204, a Calixarene Derivative that Potently Inhibits VEGF and PDGF-Stimulation of Flk-1 and PDGF Receptor Tyrosine Phosphorylation The initial approach to disrupt biologically significant protein-protein interactions such as those involving growth factors with their receptors, consisted of designing molecules that contained four synthetic peptide loops attached to a calix[4]arene scaffold (FIG. 1, reaction (a)) (Blaskovich, M. A. et al. *Nat Biotechnol*, 2000, 18:1065-70). The peptide loop components were based on a cyclic hexapeptide in which two residues are replaced by the dipeptide mimetic 3-aminomethylbenzoate modified with a 5-amino group to provide linkage to the calixarene cavity. This design allowed the synthesis of a library of calixarene derivatives having different peptide sequences in the loops and large surface areas capable of binding protein surfaces. One of the library members, GFB 111, bound PDGF and blocked its binding to PDGFR at subμM concentrations and selectively relative to other growth factors (Blaskovich, M. A. et al. *Nat Biotechnol*, 2000, 18:1065-70). The four peptide loops in GFB 111 contained negative and hydrophobic residues in the sequence GDGY (FIG. 1, reaction (a)), which match well with the positive and hydrophobic amino acids in loops I, II and III of the homodimeric PDGF, which are critical for binding to PDGFR (Oefner, C. et al. *Embo J*, 1992, 11:3921-6; Andersson, M. et al. *Growth Factors*, 1995, 12:159-64). GFB111 and similar compounds are described in U.S. Published Application No. U.S. 2003/0118589, filed Mar. 21, 2001, and International Published Application No. WO 01/70930, filed Mar. 21, 2001, which are incorporated by reference in their entirety, including all figures and tables. To improve this design, a second-generation library has been designed in which in place of the peptide loops simple, acyclic isophthalic acid groups functionalized with a wide range of acidic and hydrophobic groups ($R_1$ and $R_2$; FIG. 1, reaction (b); and Table 1) are attached to the calix[4]arene scaffold.

TABLE 1

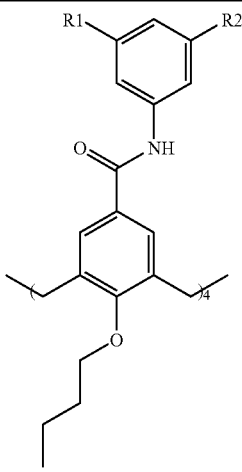

| Compound | R1 | R2 | IC$_{50}$ (uM) PDGFR | VEGFR |
|---|---|---|---|---|
| GFB201 | —C(=O)OH | —C(=O)OH | 2.62 ± 0.5 | 4.96 ± 0.34 |
| GFB202 | —C(=O)NH-CH(COOH)-CH$_2$-COOH | —C(=O)NH-CH(COOH)-CH$_2$-COOH | 1.39 ± 0.38 | 11.3 ± 2.90 |

TABLE 1-continued

| Compound | R1 | R2 | IC$_{50}$ (uM) | |
| --- | --- | --- | --- | --- |
| | | | PDGFR | VEGFR |
| GFB203 | NHAc-CH$_2$CH$_2$-COOH | NHAc-CH$_2$CH$_2$-COOH | 5.79 ± 0.72 | 19.83 ± 2.9 |
| GFB204 | Ac-OH | Ac-O-benzyl | 0.19 ± 0.06 | 0.48 ± 0.31 |
| GFB205 | N-Ac-Asp | N-Ac-Tyr | 3.1 ± 0.71 | 5.86 ± 0.68 |
| GFB206 | N-Ac-Asp | NHAc-CH$_2$CH$_2$-COOH | 2.58 ± 0.21 | >10<br>>30 |
| GFB207 | N-Ac-Tyr | NHAc-CH$_2$CH$_2$-COOH | 3.47 ± 1.87 | 18.43 ± 2.72 |
| GFB208 | N-Ac-Tyr(OCH$_2$COOH) | NHAc-CH$_2$CH$_2$-COOH | 0.84 ± 0.06 | >30<br>>10 |

TABLE 1-continued
| Compound | R1 | R2 | IC$_{50}$ (uM) PDGFR | IC$_{50}$ (uM) VEGFR |
|---|---|---|---|---|
| GFB209 | 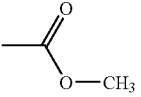 |  | 2.91 ± 2.05 | 5.58 ± 4.11 |
| GFB210 | 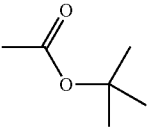 |  | 0.35 ± 0.31 | 4.54 ± 0.55 |
| GFB211 | 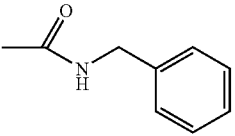 | 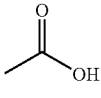 | 1.34 ± 0.32 | 12.95 ± 0.49 |
| GFB212 | 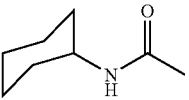 | 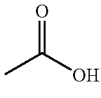 | 0.29 ± 0.08 | >10<br>>10<br>>10 |
| GFB213 | 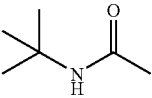 | 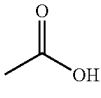 | 0.57 ± 0.06 | 0.85 ± 0.44 |
| GFB214 | 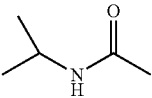 | 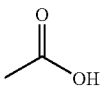 | 0.17 ± 0.02 | >10<br>>10<br>>10 |
| GFB215 | 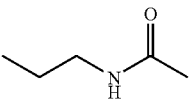 | 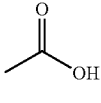 | 0.21 ± 0.13 | >10<br>>10<br>>10 |
| GFB216 | 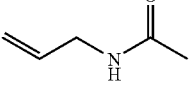 | | 0.15 ± 0.01 | >10<br>>10<br>>10 |

TABLE 1-continued

| Compound | R1 | R2 | IC$_{50}$ (uM) PDGFR | VEGFR |
|---|---|---|---|---|
| GFB217 | *tert-butyl ester* (OC(O)OC(CH$_3$)$_3$) | *benzyl ester* (OC(O)OCH$_2$Ph) | >10<br>>10 | >10<br>>10<br>>10 |
| GFB218 | COOH | 4-pyridyl acetamide | 0.54 ± 0.15 | >10<br>>10<br>>10 |
| GFB219 | COOH | 1-naphthyl acetamide | 0.53 ± 0.15 | >10<br>>10<br>>10 |

To evaluate this library for molecules capable of preventing PDGF and VEGF binding to their receptors, their ability to disrupt PDGF- and VEGF-stimulated receptor tyrosine phosphorylation as described under Materials and Methods was first determined. From the 19 compounds in the library GFB204 was identified (where R$_1$ is a carboxylic acid and R$_2$ a benzyl ester) as a potent inhibitor of both VEGFR and PDGFR tyrosine phosphorylation (Table 1) with IC$_{50}$ values of 190 nM (PDGF) and 480 nM (VEGF). All the library members having at least four carboxylic groups inhibited PDGF signaling at low μM concentrations (IC$_{50}$<6 μM), while the only compound lacking acidic groups (GFB217) did not have a significant activity. Analysis of the data in Table 1 revealed that all the potent inhibitors (having IC$_{50}$<0.6 μM) contain R$_1$=COOH and R$_2$=hydrophobic ester or amide. GFB211, where R$_2$=benzylamide, has an activity only slightly lower (IC$_{50}$=1.34±0.32 μM) than GFB204, while GFB209, (R$_2$=methyl ester) is less potent (IC$_{50}$=2.9±2.05 μM). These data suggest that the structure of the hydrophobic substituents is not crucial for PDGF signaling inhibition, as long as they are larger than a methyl group. Compounds having aromatic and aliphatic groups are equally active and the more stable amides have similar activity to their ester analogs.

In contrast, the calixarene derivatives containing amino acid substituents (i.e. GFB202, GFB203, GFB205, GFB206, GFB207 and GFB208) show in general lower activity (IC$_{50}$ in the range 1-6 μM). This may be due either to a change in the ratio of ionic to hydrophobic groups on the scaffold (these derivatives have 8-16 carboxylic acids and only 0-4 hydrophobic substituents) or to a non-optimal distance between them. Moreover, the presence of acidic groups on the isophthalic spacer seems to be more important than the presence of hydrophobic substituents: GFB201, GFB202, GFB203, and GFB206 lack hydrophobic groups in the R$_1$ and R$_2$ positions but are more potent than GFB217, which has no carboxylate groups. Possibly, the isophthalic acid groups themselves provide a hydrophobic area that interacts with the hydrophobic regions of the receptors binding domain of PDGF.

Finally, it is important to note that the most active compounds in the study have exactly one carboxylic acid and one hydrophobic group on the four isophthalic components within the scaffold consistent with previous studies which led to the identification of GFB111 (Blaskovich, M. A. et al. *Nat*

*Biotechnol,* 2000, 18:1065-70). SAR studies also revealed that the characteristics necessary in this series for inhibition of VEGF-stimulated Flk-1 tyrosine phosphorylation are much more stringent. Indeed, besides GFB204 ($IC_{50}$=0.48±0.31 µM), only one other potent compound, GFB213, inhibited Flk-1 tyrosine phosphorylation with an $IC_{50}$ value of 0.85±0.44 µM (Table 1). The factors that determine the inhibition activity towards VEGF signaling are difficult to infer from the data in Table 1.

Figure 2A:
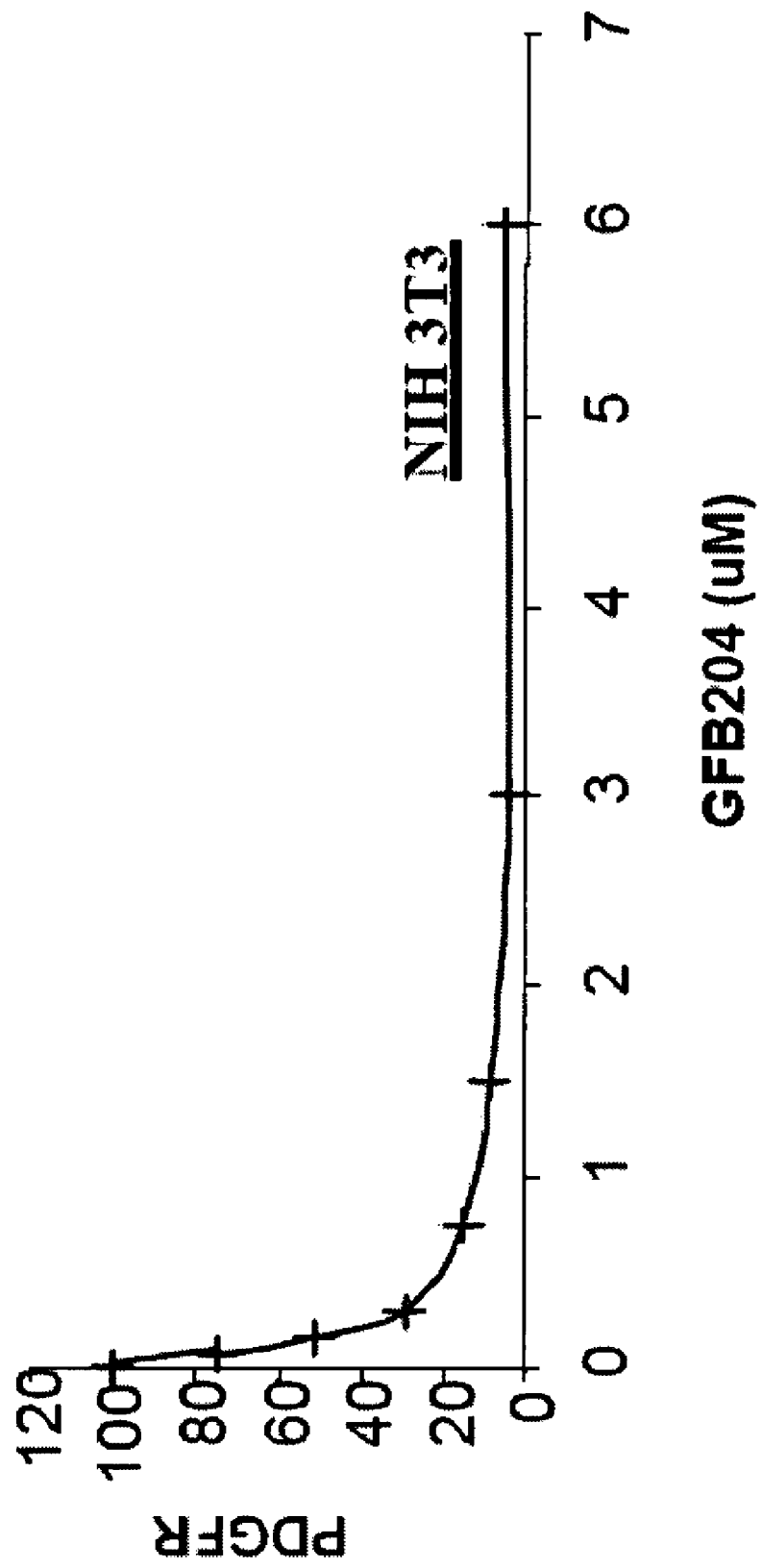
FIGS. 2A-2C show that GFB204 inhibits $^{125}$I-VEGF and $^{125}$I-PDGF but not $^{125}$I-EGF binding to their receptors in mouse fibroblasts. Flk-1/NIH 3T3, NIH 3T3 and EGFR/NIH 3T3 cells were incubated with $^{125}$I-VEGF, $^{125}$I-PDGF and $^{125}$I-EGF (50,000 cpm/well) respectively, along with increasing concentrations of GFB204. Cells were incubated at 4° C. for 0.5 hours, then washed three times with PBS and three times with lysis buffer prior to determining $^{125}$I counts as described under Materials and Methods. An excess of cold VEGF, PDGF, and EGF was used to obtain non-specific binding levels.
Figure 2B:
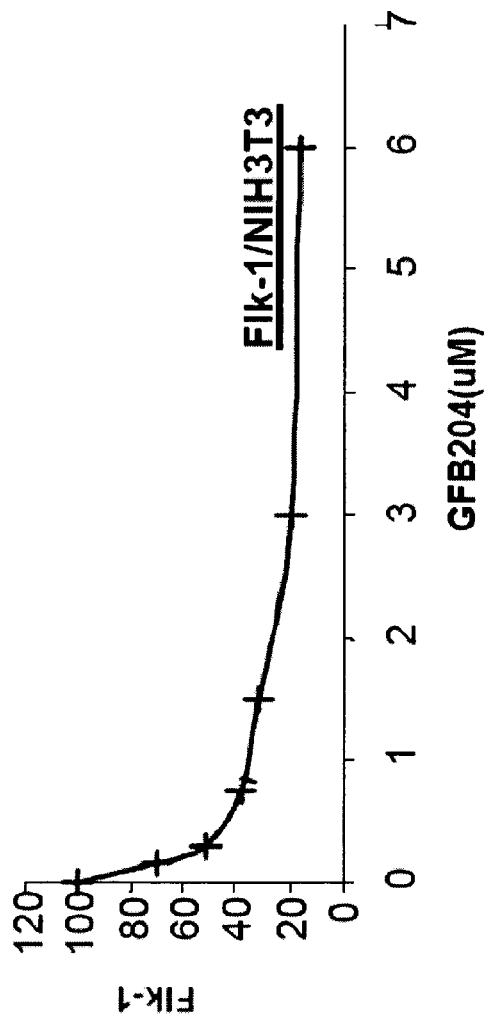
Figure 2C:
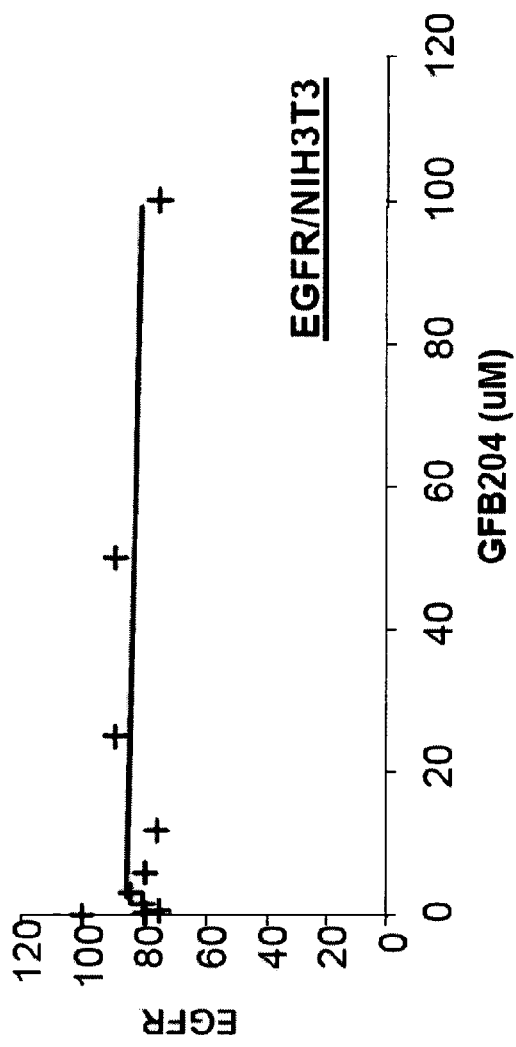
Figures 2D, 2E:
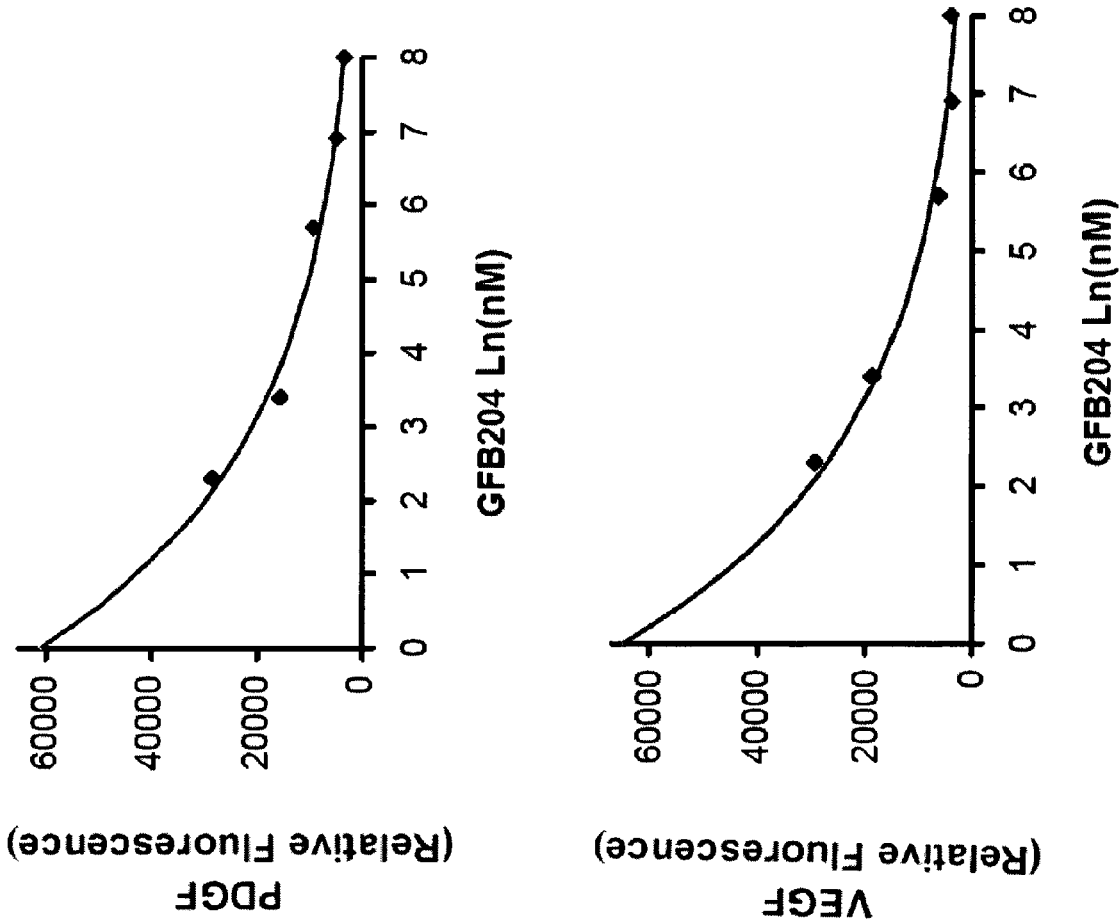
FIGS. 2D and 2E illustrate that GFB-204 binds PDGF and VEGF as indicated by growth factor tryptophan when increased amounts of GFB204 were added to PDGF and VEGF, respectively. The fluorescence was monitored by excitation at 295 nm and 228 nm, respectively, and emission at 334 nmn.

GFB204 binds both PDGF and VEGF. The ability of GFB204 to bind both VEGF and PDGF was demonstrated by fluorescence titration curves. Both VEGF and PDGF contain tryptophans that fluoresce at 334 nM when excited at 294 nM. FIGS. 2D and 2E show that increasing concentrations of GFB-204 decreased the ability of PDGF and VEGF to fluoresce in a concentration dependent manner.

EXAMPLE 2

GFB204 Inhibits VEGF and PDGF but not EGF Binding to their Respective Receptors

The ability of GFB204 to inhibit PDGF and VEGF-stimulated receptor tyrosine phosphorylation suggested that GFB204 either disrupts ligand/receptor binding, receptor dimerization or receptor tyrosine kinase activity. Therefore, it was determined whether GFB204 inhibits the interaction between PDGF and VEGF and their respective receptors but not other growth factors. To this end, the present inventors evaluated the ability of GFB204 to block [I-125]-PDGF, [I-125]-VEGF and [I-125]EGF binding to their receptor on NIH 3T3 cells (PDGF), NIH 3T3 cells overexpressing human Flk-1 (VEGF) and human EGFR (EGF) as described under Materials and Methods. GFB204 effectively inhibited the binding of [I-125]PDGF and [I-125]-VEGF to their receptors with $IC_{50}$ values of 154+/−1.0 nM and 469 +/−94 nM, respectively (FIGS. 2A-2C). In contrast, [I-125]EGF binding to its receptor was not affected by GFB204 with concentrations as high as 100 µM. Thus, GFB204 is more selective for PDGF and VEGF over EGF.

EXAMPLE 3

Figure 3A:
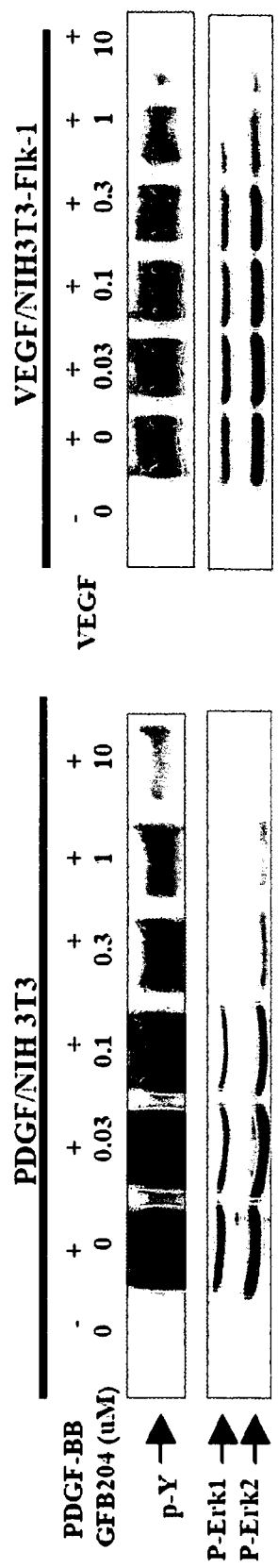
FIGS. 3A and 3B show the effect of GFB204 on growth factor stimulated Erk1, Erk2, Akt, and STAT3 phosphorylation. GFB204 inhibits VEGF and PDGF stimulation of Flk-1 tyrosine phosphorylation and Erk1/Erk2 phosphorylation (FIG. 3A). NIH 3T3 cells or Flk-1/NIH 3T3 cells were treated with increasing concentrations of GFB204 for 5 minutes prior to stimulation with PDGFBB (10 ng/ml) or VEGF (50 ng/ml), respectively, for 10 minutes. The cells were then lysed and processed for SDS-PAGE Western blotting with an antibody specific for phosphotyrosine-Flk-1 or anti-phosphotyrosine for PDGFR tyrosine phosphorylation or phospho-Erk1/2. GFB204 effects on growth factor-stimulated Erk1, Erk2, Akt and STAT3 phosphorylation (FIG. 3B). NIH 3T3, Flk-1/NIH 3T3, IGF-R/NIH 3T3 or EGFR/NIH 3T3 cells were treated with GFB204 (10 µM) prior to stimulation with PDGF (NIH 3T3) VEGF (Flk-1/NIH 3T3), EGF (EGFR/NIH 3T3), bFGF (NIH 3T3) or IGF-1 (IGF-1R/NIH 3T3). The cells were then harvested and processed for SDS-PAGE Western blotting with antibodies specific for phospho-Erk1/2, phospho-Akt and phospho-STAT3.
Figure 3B:
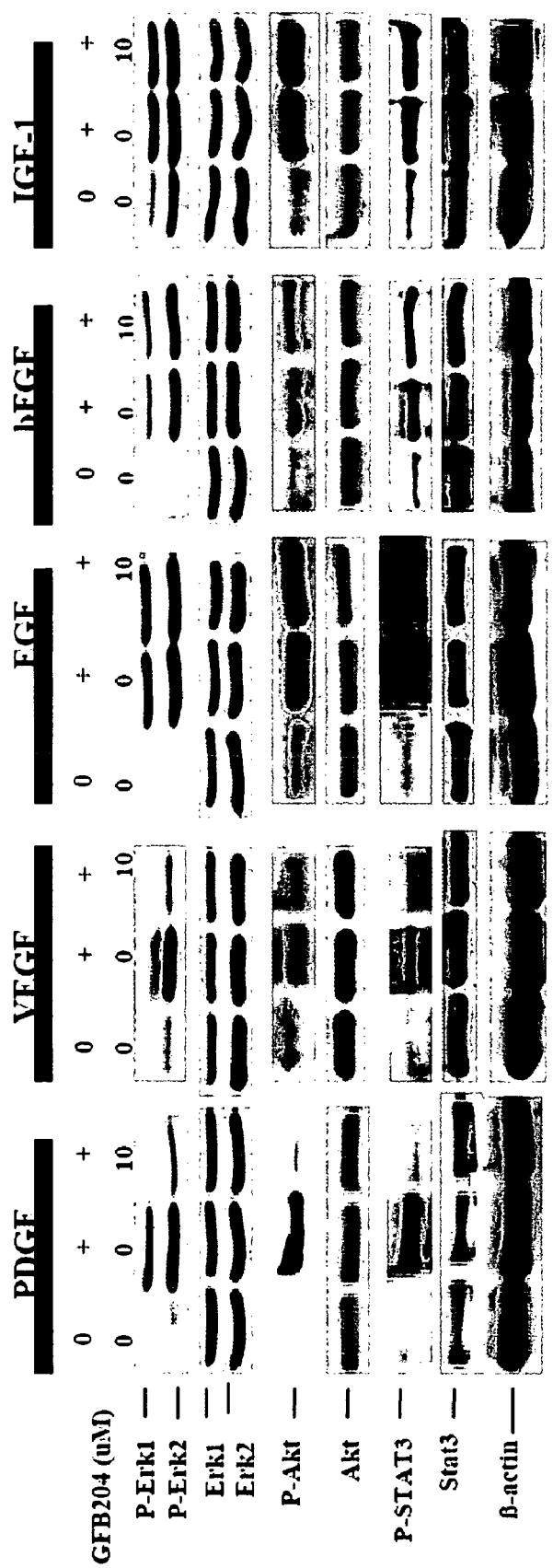

GFB204 Disrupts PDGF- and VEGF- but not EGF-, bFGF- or IGF-1 Stimulation of Erk1, Erk2, Akt and STAT3 Phosphorylation To further document the selectivity of GFB204 for PDGF and VEGF over other growth factors, the present inventors determined the ability of GFB204 to block growth factor stimulation of the kinases Erk1, Erk2 and Akt as well as the signal transducer and activator of transcription STAT3. To this end, NIH 3T3 cells (PDGF and bFGF) or NIH 3T3 cells that overexpress Flk-1 (VEGF), EGFR (EGF) or IGF-R (IGF-1) were starved and stimulated with the corresponding growth factor in the presence or absence of GFB204, and the cells were processed for anti-phosphotyrosine (PDGF and VEGF) and for anti-phospho-Erk1/2, Akt and STAT3 (PDGF, VEGF, EGF, bFGF and IGF-1) Western immunoblotting as described under Materials and Methods. FIG. 3A shows that, as described in Table 1, treatment of starved cells with PDGF or VEGF resulted in potent stimulation of receptor tyrosine phosphorylation and that treatment with GFB204 inhibited this stimulation with $IC_{50}$ values of 190 nM and 480 nM, respectively. Similarly, PDGF- and VEGF-stimulation of Erk1 Erk2 was also inhibited with similar $IC_{50}$ values. Furthermore, this inhibition was selective in that GFB204 blocked PDGF- and VEGF- but had little effect on EGF-, bFGF- and IGF-1-stimulation of the phosphorylation of Erk1, Erk2, Akt and STAT3 (FIG. 3B).

EXAMPLE 4

Figure 4B:
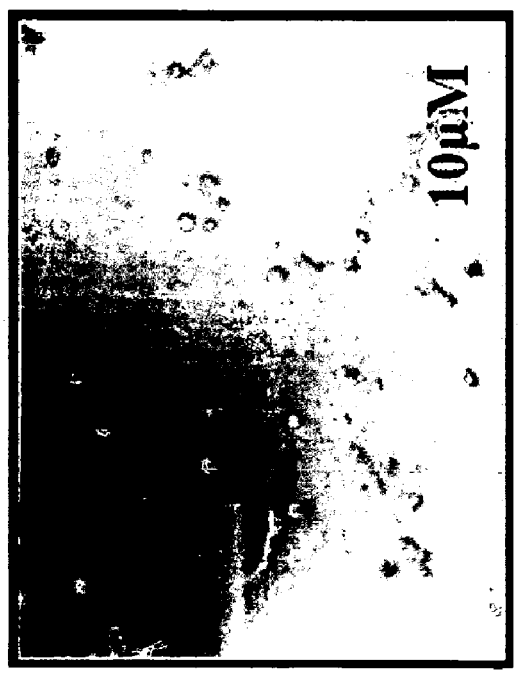
FIGS. 4A-4C show the effects of GFB204 on angiogenesis in vitro. GFB204 inhibits capillary network formation in a dose-response manner (FIG. 4C). Human middle cerebral artery endothelial cells (5×10$^4$) were seeded onto Matrigel and the cells were incubated with VEGF in the presence (FIG. 4B) or absence (FIG. 4A) of GFB204 as described under Materials and Methods.
Figure 4A:
Figure 4C:
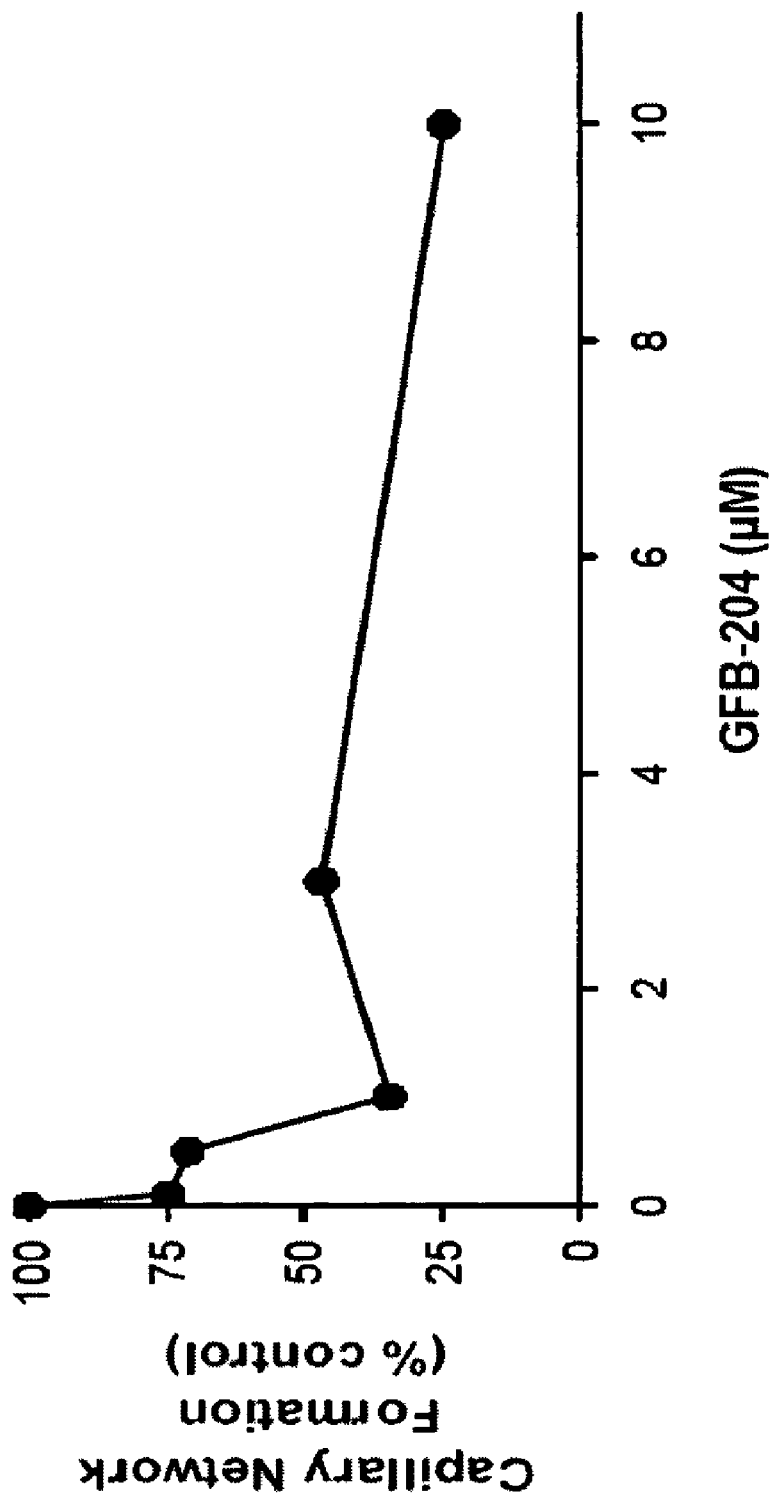

GFB204 Inhibits Angiogenesis In Vitro and In Vivo and Suppresses the Growth of Human Tumors in Nude Mice The ability of GFB204 to inhibit potently and selectively PDGF and VEGF/ligand receptor binding and subsequent signaling prompted the present inventors to determine whether this agent could inhibit angiogenesis, in vitro and in vivo and subsequently inhibit tumor growth. First, it was determined if GFB204 could inhibit angiogenesis in vitro by evaluating its ability to suppress VEGF-induced human brain endothelial capillary network formation as described under Materials and Methods. GFB204 was highly efficient at inhibiting VEGF-induced capillary network formation with an $IC_{50}$ value of 700 nM (FIG. 4C). The ability of GFB204 to inhibit human brain endothelial cell migration as described under Materials and Methods was determined next. GFB204 inhibited VEGF-induced endothelial cell migration through matrigel pores into the lower chamber with an $IC_{50}$ value of 600 nM (FIG. 4B).

Figure 5B:
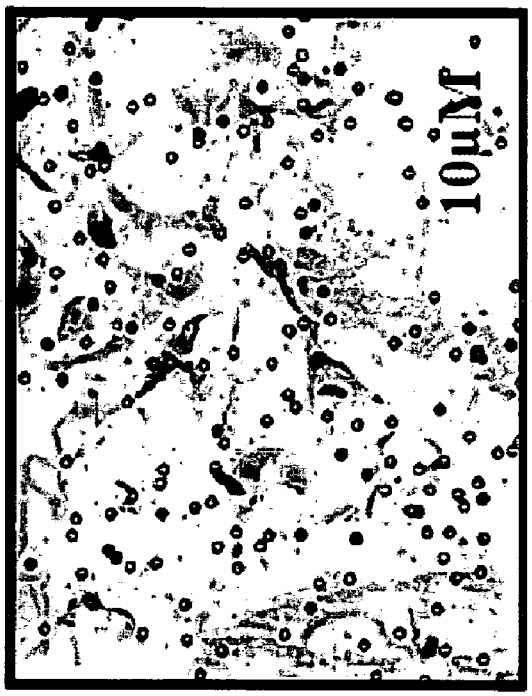
FIGS. 5A-5C illustrates that GFB204 potently inhibits VEGF-dependent human brain endothelial cell migration in vitro. Migration of adult human brain endothelial cells was evaluated using a modified Boyden chamber assay as described in Materials and Methods. Vehicle control (FIG. 5A) or GFB204 (FIG. 5B) was added to 2% FBS-containing medium in the outer chamber, and the number of migrated cells to the VEGF-containing lower chamber was determined after an 18-hour incubation (FIG. 5C).
Figure 5A:
Figure 5C:
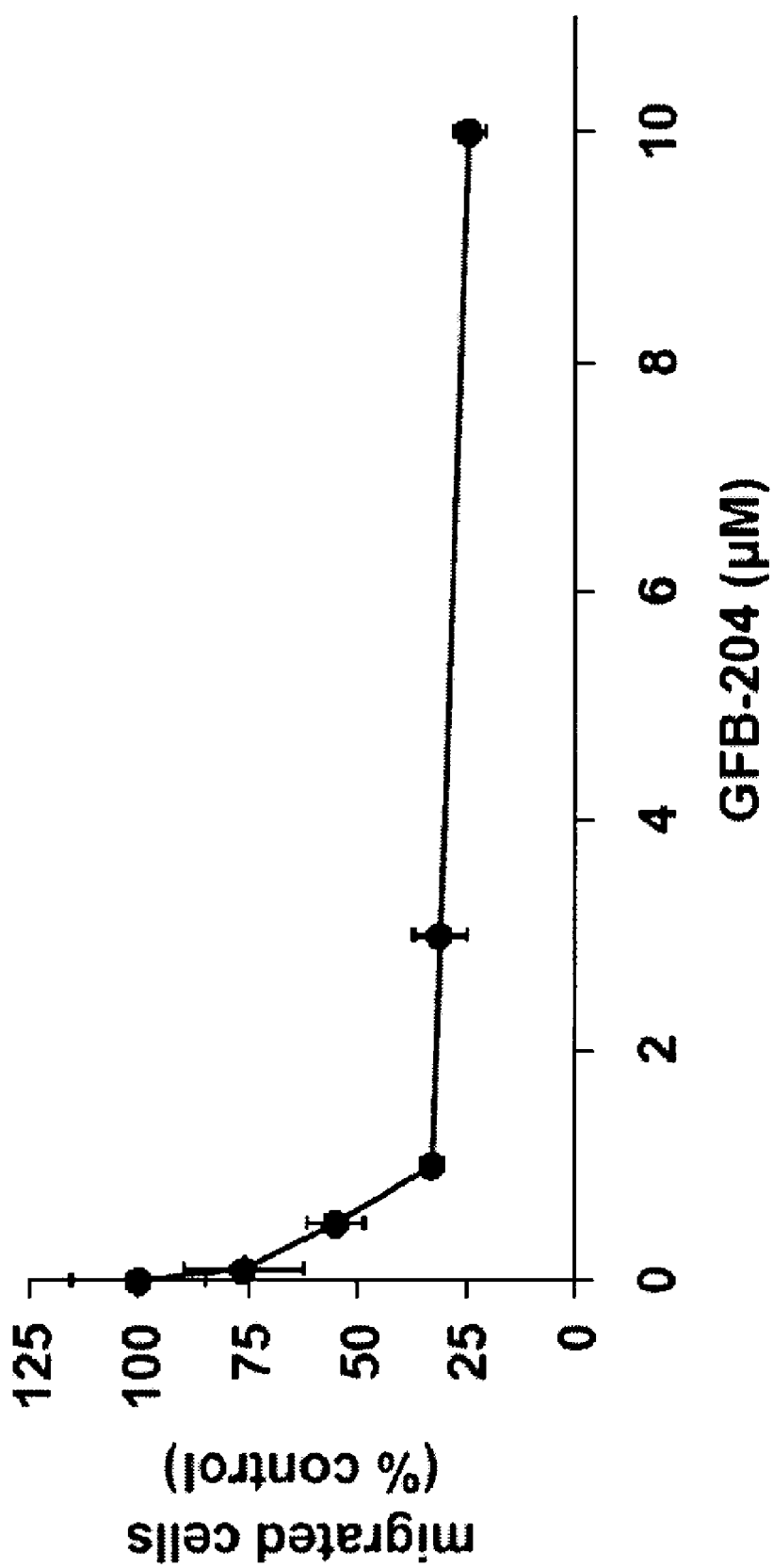
Figure 6:
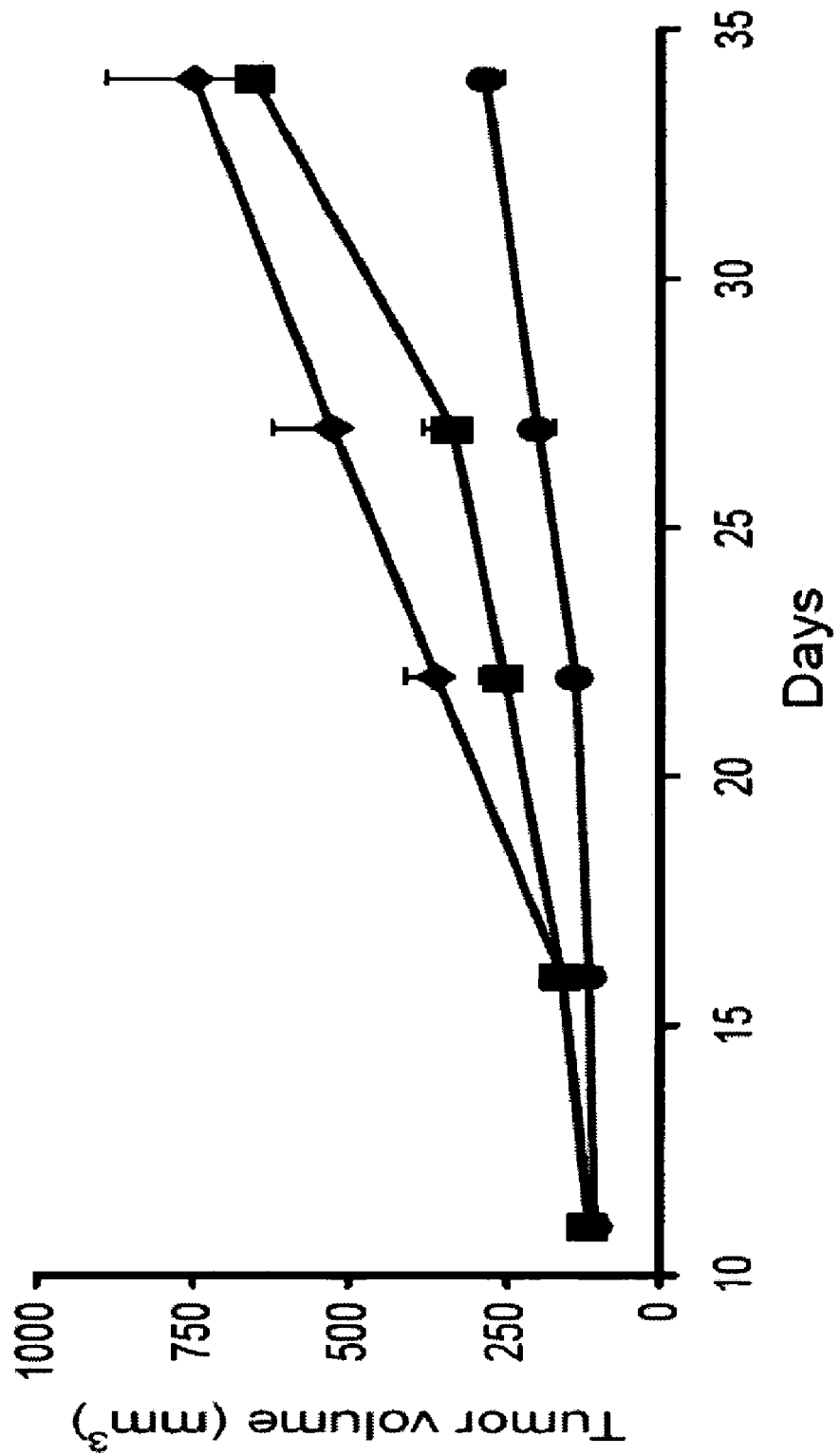
FIG. 6 illustrates that GFB204 inhibits A-549 xenografts growth in nude mice (FIG. 6). A-549 cells were implanted into the flanks of nude mice and when the tumors reached an average size of about 100 mm$^3$, the mice were randomized and treated either with vehicle (♦) or GFB204 at 1 mg/kg (■) and 5 mg/kg (●), and tumor sizes measured as described under Materials and Methods. Tumors were processed two hours after the last i.p. injection for CD31 IHC staining as described under Materials and Methods.
Figure 7B:
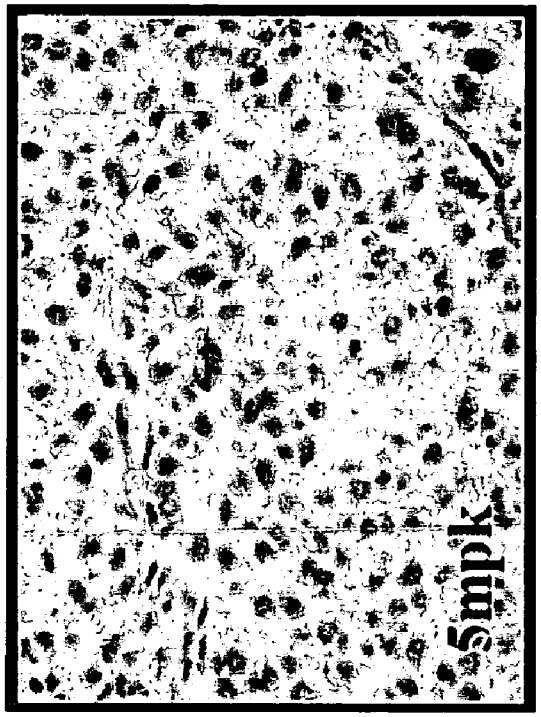
FIGS. 7A-7B illustrates CD31 IHC staining as described under Materials and Methods for tumors processed two hours after the last i.p. injection for a control (FIG. 7A) and GFB204 (FIG. 7B). Quantification of microvessels density (400×) was determined as described under Materials and Methods. SE, standard error.
Figure 7A:

The ability of GFB204 to inhibit VEGF and PDGF binding to their receptors and subsequent signaling coupled with its ability to inhibit VEGF-induced endothelial cell migration and capillary network formation suggested that GFB204 might inhibit angiogenesis and tumorigenesis in whole animals. Therefore, it was next evaluated whether GFB204 is able to suppress tumor growth and angiogenesis in vivo by implanting human lung cancer A-549 cells s.c. in nude mice. When tumors reached an average size of 100 mm$^3$, the mice were treated with either vehicle or GFB204 and 3 weeks later the tumors were removed and processed for CD31 immunostaining to determine GFB204 anti-angiogenic effects as described under Materials and Methods. Tumors from control animals grew to an average size of 749±111 mm$^3$ (FIG. 6). In contrast, tumors from GFB204-treated animals grew to an average size of only 650±114 mm$^3$ (GFB204; 1 mg/kg), and 284±108 mm$^3$ (GFB204; 5 mg/kg), respectively. Thus, treatment with GFB204 resulted in a statistically significant ($p<0.05$), tumor growth inhibition at 5 mg/kg (73%), but not at 1 mg/kg (15%). Tumor sections from GFB204 treated animals show a significant inhibition of CD31 staining (FIGS. 5A-5C). Quantification of microvessels at field magnification (400×) indicated that tumors from vehicle-treated mice contained 11.3±1.9 microvessels whereas those from mice treated with GFB204 (5 mg/Kg) had only 2.6±0.9 microvessels. Taken together, the results clearly demonstrated that GFB204 inhibits A-549 xenografts tumor growth and angiogenesis in vivo.

The strict requirement and stringent dependence of tumor growth on angiogenesis has prompted many investigators to design strategies for cancer therapy by disrupting angiogenesis resulting in deprivation of cancer cells of nutrients and essentially tumor starvation (Zhang, W. et al. *Angiogenesis,* 2002, 5:35-44; Ferrara, N. *Semin Oncol,* 2002, 29:10-4; Jain, R. K. *Semin Oncol,* 2002, 29:3-9; Morin, M. J. *Oncogene,* 2000, 19:6574-83; Miao, R. Q. et al. *Blood,* 2002, 100:3245-52; Laird, A. D. et al. *Cancer Res,* 2000, 60:4152-60; Wedge, S. R. et al. *Cancer Res,* 2000, 60:970-5; Relf, M. et al. *Cancer Res,* 1997, 57:963-9; Huang, J. et al. *Proc Natl Acad Sci USA,* 2003, 100:7785-90; Blaskovich, M. A. et al. *Nat Biotechnol,* 2000, 18:1065-70). Although targeting angiogenesis as an approach to cancer therapy was suggested decades ago, it is only very recently that the first drug designed to target a step in the complex process of angiogenesis has been approved by the FDA (Ferrara, N. *Semin Oncol,* 2002, 29:10-4). Indeed, AVASTIN, a humanized anti-VEGF monoclonal antibody has shown activity against metastatic colon cancer. Though pivotal for providing proof of concept for targeting angiogenesis in humans, this approach has not been fully exploited. One improvement that is sought after is to design strategies that simultaneously target different steps in the angiogenic process (Bergers, G. et al. *J Clin Invest,* 2003, 111: 1287-95; Relf, M. et al. *Cancer Res,* 1997, 57:963-9; Huang, J. et al. *Proc Natl Acad Sci USA,* 2003, 100:7785-90). The present inventors have developed a novel synthetic pharmacological agent that inhibits the function of both VEGF and PDGF, growth factors that have been shown to mediate initiation and maintenance of new blood vessels, respectively (Bergers, G. et al. *J Clin Invest,* 2003, 111:1287-95; Dvorak, H. F. *J Clin Oncol,* 2002, 20:4368-80; Ferrara, N. *Curr Top Microbiol Immunol,* 1999, 237:1-30; Dvorak, H. F. et al. *Curr Top Microbiol Immunol,* 1999, 237:97-132; Eriksson, U. and Alitalo, K. *Curr Top Microbiol Immunol,* 1999, 237:41-57). This is the first report of an agent that inhibits the binding of both VEGF and PDGF to their receptors and subsequently suppresses tyrosine phosphorylation and downstream signaling pathways (Erk, Akt and STAT3). GFB204 also blocked potently the ability of endothelial cells to migrate ($IC_{50}=600$ nM) as well as their ability to form capillaries in vitro ($IC_{50}=700$ nM). In vivo, treatment of mice bearing human tumors s.c. led to inhibition of blood vessel formation around the tumor mass as well as inhibition of tumor growth. Although GFB204 potently inhibited both VEGF and PDGF binding to their receptors (200-500 nM) it was not a non-specific disrupter of all of ligand/receptor binding since EGF binding to its receptor was not affected at doses as high as 100 μM. Further support for selectivity was provided by demonstrating that GFB204 inhibited the activation of Erk1, Erk2, Akt and STAT3 by PDGF and VEGF but not by EGF, bFGF or IGF-1.

Identification of calix[4]arene derivatives capable of blocking binding of both VEGF and PDGF to their receptors is an entirely novel approach to targeting receptor tyrosine kinase signaling. Although the anti-VEGF antibody AVASTIN also blocks VEGF binding to its receptor (Zhang, W. et al. *Angiogenesis,* 2002, 5:35-44; Ferrara, N. *Semin Oncol,* 2002, 29:10-4), there are apparently no other agents that block binding of both PDGF and VEGF to their receptors. Furthermore, the advantage of GFB204 over AVASTIN is that GFB204 is a much smaller molecule that can be easily synthesized at low cost, unlike the laborious and expensive methods involved in generating antibodies for therapeutic purposes. Although prior to this report there were no dual inhibitors of VEGF and PDGF binding to their receptors, dual inhibitors of VEGF and PDGF receptor tyrosine kinases have been made and some are in clinical trials (Kerbel, R. S. *Carcinogenesis,* 2000, 21:505-15; Jain, R. K. *Semin Oncol,* 2002, 29:3-9; Morin, M. J. *Oncogene,* 2000, 19:6574-83; Miao, R. Q. et al. *Blood,* 2002, 100:3245-52; Laird, A. D. et al. *Cancer Res,* 2000, 60:4152-60; Wedge, S. R. et al. *Cancer Res,* 2000, 60:970-5).

There are distinct differences between these ATP mimics and GFB204. While the target for GFB204 is the ligand/receptor interaction that occurs extracellularly on the outer cell surface, ATP mimics target the tyrosine kinase domains of the receptors that are intracellular. Therefore, unlike GFB204, kinase inhibitors must enter cells to reach their target. Furthermore, most tyrosine kinase inhibitors target the ATP binding site, variations of which are ubiquitous in cells. Therefore, the outcome of treating patients with GFB204 may be very different from that of treating patients with an ATP mimic that targets both PDGF and VEGF receptor tyrosine kinases. Advanced preclinical studies are underway in preparation for an IND application for phase I testing of GFB204 in humans.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A growth factor binding compound according to structure (I):

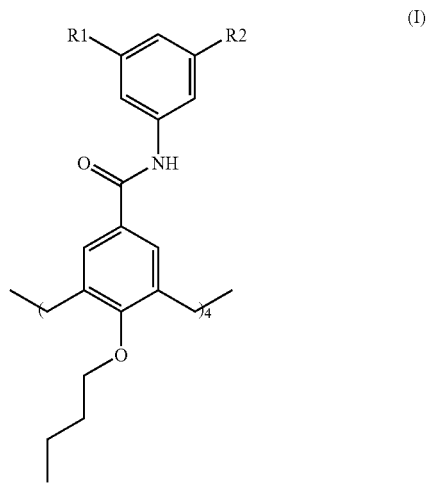

wherein each R1 is independently selected from the group consisting of:

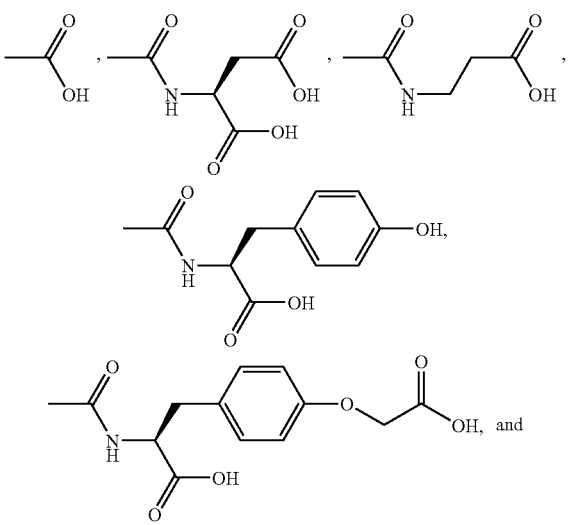

-continued
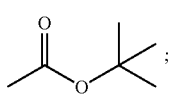
wherein each R2 is independently selected from the group consisting of:
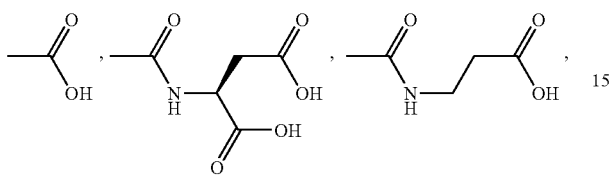
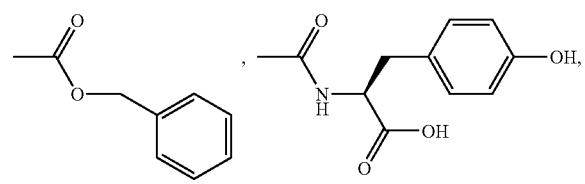
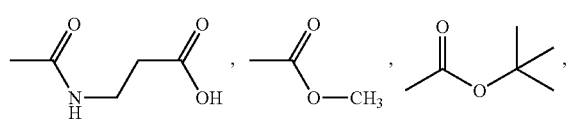
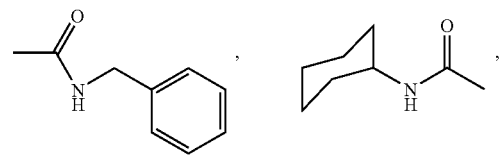
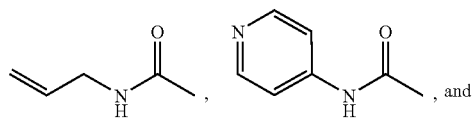
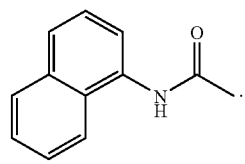
2. The growth factor binding compound according to claim 1, wherein the compound is selected from the group consisting of compounds according to structure (I), wherein:
each R1 is
and each R2 is
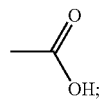
each R1 is
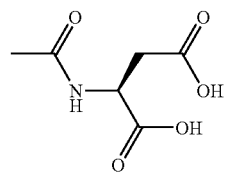
and each R2 is
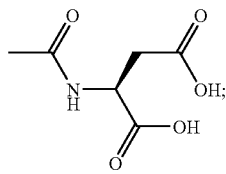
each R1 is
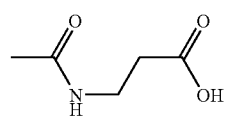
and each R2 is
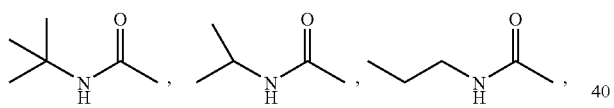
each R1 is
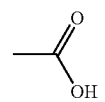
and each R2 is
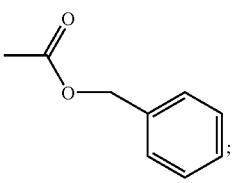

each R1 is
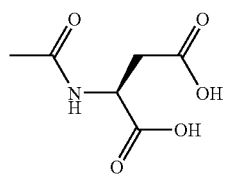
and each R2 is
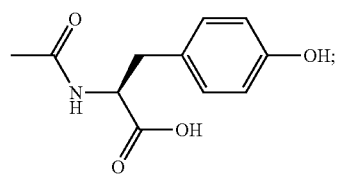
each R1 is
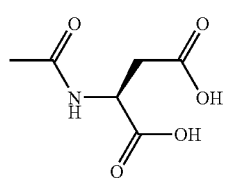
and each R2 is
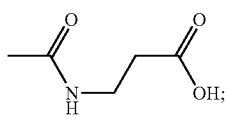
each R1 is
each R1 is
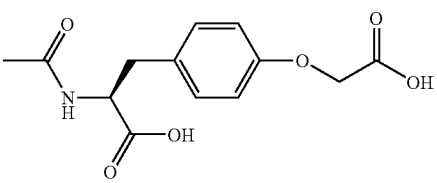
and each R2 is
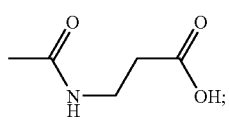
each R1 is
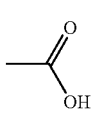
and each R2 is
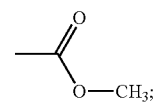
each R1 is
and each R2 is
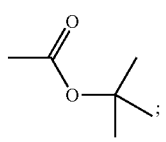
each R1 is

and each R2 is
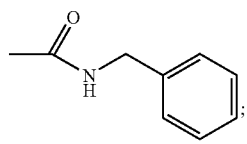
each R1 is
and each R2 is
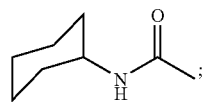
each R1 is
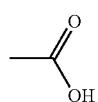
and each R2 is
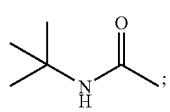
each R1 is
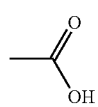
and each R2 is
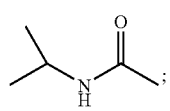
each R1 is
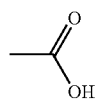
and each R2 is
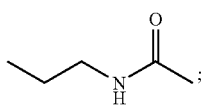
each R1 is
and each R2 is
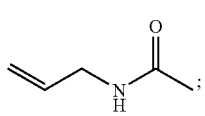
each R1 is
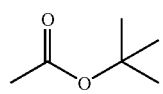
and each R2 is
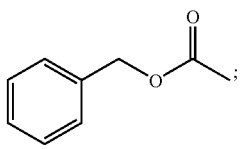
each R1 is
and each R2 is
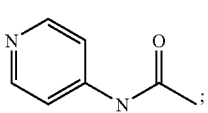
and each R1 is

and each R2 is

3. The growth factor binding compounds according to claim 1, wherein the compound is capable of binding to platelet derived growth factors, vascular endothelial growth factor, or a mixture of any of the foregoing.

4. A pharmaceutical composition comprising one or more growth factor binding compounds of claim 1 or a pharmaceutically acceptable salt of any of the growth factor binding compounds, and a pharmaceutically acceptable carrier.

5. The pharmaceutical composition according to claim 4, wherein each of the growth factor binding compounds are selected from the group consisting of compounds according to structure (I), wherein:

each R1 is

and each R2 is

each R1 is

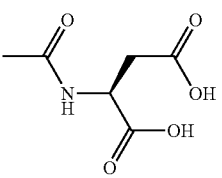

and each R2 is

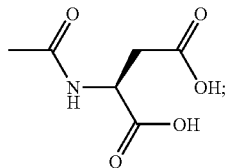

each R1 is

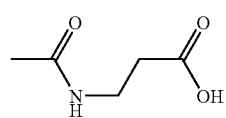

and each R2 is

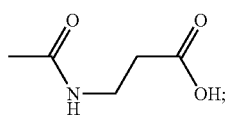

each R1 is

and each R2 is

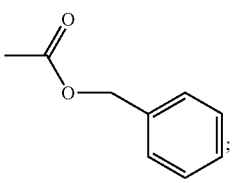

each R1 is

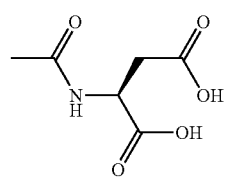

and each R2 is
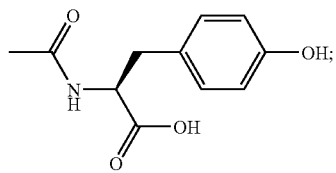
each R1 is
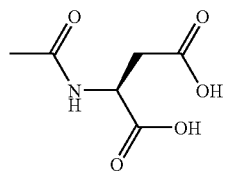
and each R2 is
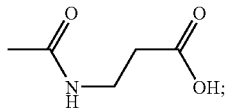
each R1 is
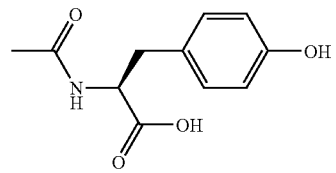
and each R2 is
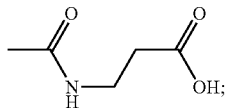
each R1 is
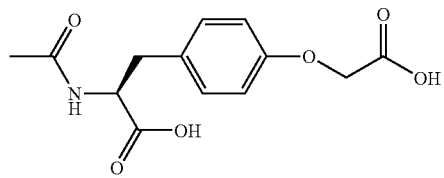
and each R2 is
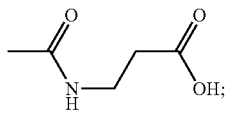
each R1 is
and each R2 is
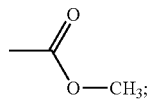
each R1 is
and each R2 is
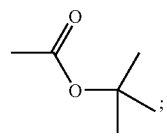
each R1 is
and each R2 is
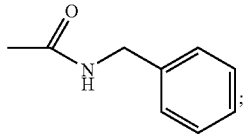
each R1 is
and each R2 is
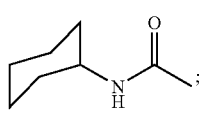

each R1 is

and each R2 is

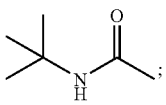

each R1 is

and each R2 is

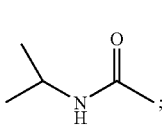

each R1 is

and each R2 is

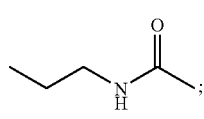

each R1 is

and each R2 is

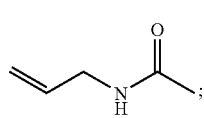

each R1 is

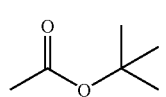

and each R2 is

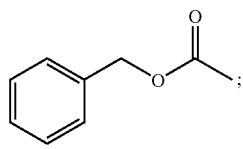

each R1 is

and each R2 is

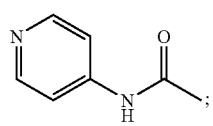

and each R1 is

and each R2 is

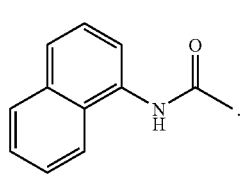

6. The pharmaceutical composition according to claim 4, wherein each of the growth factor binding compounds are capable of binding to platelet derived growth factors, vascular endothelial growth factor, or a mixture of any of the foregoing.

7. The growth factor compound of claim 1, wherein each R1 is:

and each R2 is:

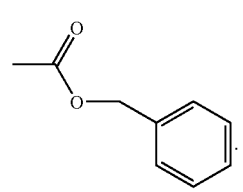

8. The pharmaceutical composition according to claim 4, wherein each R1 is:
and each R2 is:
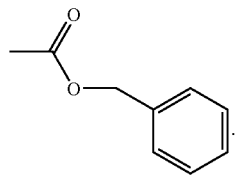
* * * * *

UNITED STATES PATENT AND TRADEMARK OFFICE
CERTIFICATE OF CORRECTION

PATENT NO. : 7,482,483 B2
APPLICATION NO. : 11/044980
DATED : January 27, 2009
INVENTOR(S) : Said Sebti et al.

It is certified that error appears in the above-identified patent and that said Letters Patent is hereby corrected as shown below:

In the Specification, the following errors are corrected:

Column 6, line 15, " 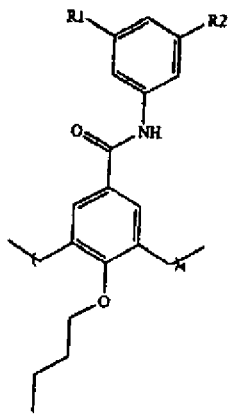 " should read -- 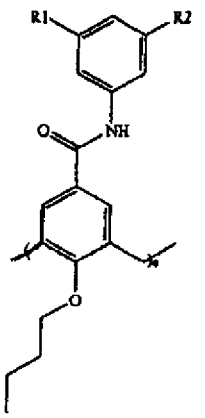 --.

Column 7, line 1, " 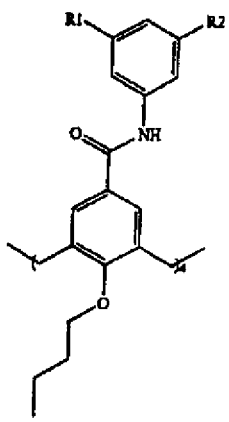 " should read -- 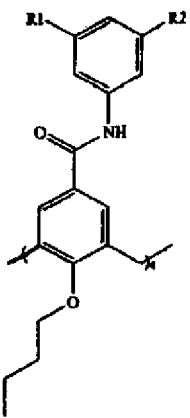 --.

// UNITED STATES PATENT AND TRADEMARK OFFICE
CERTIFICATE OF CORRECTION

PATENT NO. : 7,482,483 B2
APPLICATION NO. : 11/044980
DATED : January 27, 2009
INVENTOR(S) : Said Sebti et al.

It is certified that error appears in the above-identified patent and that said Letters Patent is hereby corrected as shown below:

Column 9, line 1, " 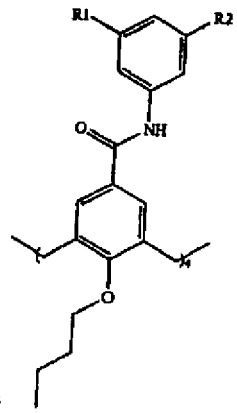 " should read -- 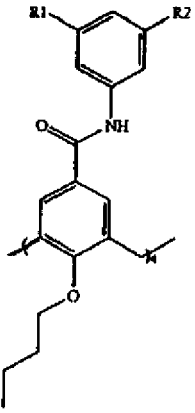 --.

Column 13, line 30, (Table 1) " 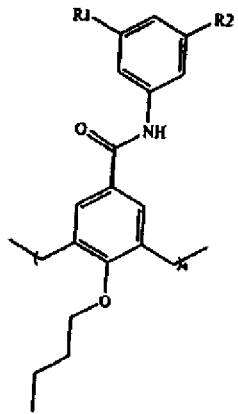 " should read -- 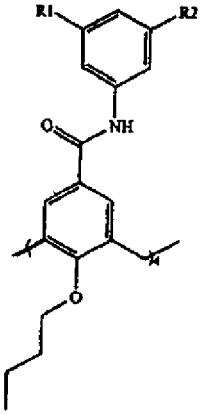 --.

Column 15, line 1, (Table 1) " 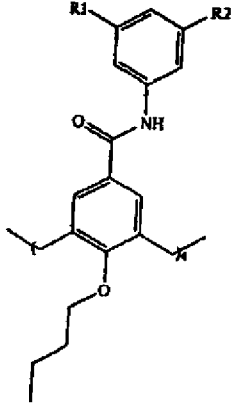 " should read -- 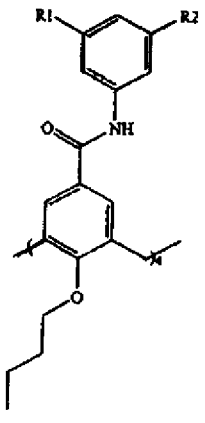 --.

UNITED STATES PATENT AND TRADEMARK OFFICE
CERTIFICATE OF CORRECTION

PATENT NO. : 7,482,483 B2
APPLICATION NO. : 11/044980
DATED : January 27, 2009
INVENTOR(S) : Said Sebti et al.

It is certified that error appears in the above-identified patent and that said Letters Patent is hereby corrected as shown below:

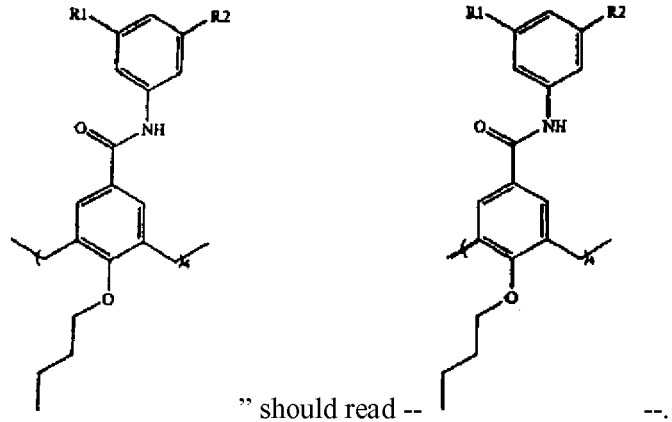

Column 17, line 1, (Table 1) " " should read -- --.

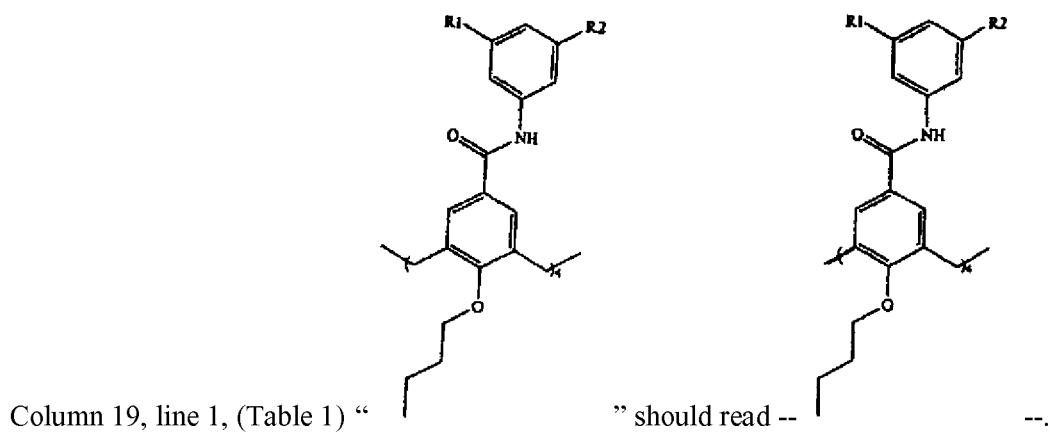

Column 19, line 1, (Table 1) " " should read -- --.

UNITED STATES PATENT AND TRADEMARK OFFICE
CERTIFICATE OF CORRECTION

PATENT NO. : 7,482,483 B2
APPLICATION NO. : 11/044980
DATED : January 27, 2009
INVENTOR(S) : Said Sebti et al.

It is certified that error appears in the above-identified patent and that said Letters Patent is hereby corrected as shown below:

In the Claims, the following errors are corrected:

Claim 1, Column 24, line 25 " 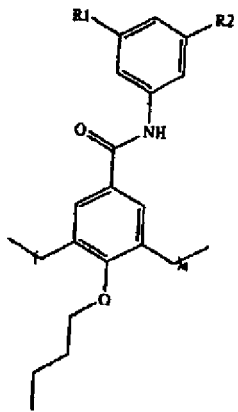 " should read -- 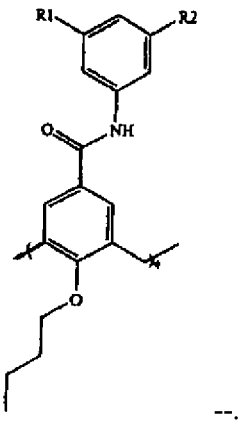 --.

Signed and Sealed this

Twenty-second Day of September, 2009

David J. Kappos
*Director of the United States Patent and Trademark Office*